United States Patent
Sievernich et al.

(10) Patent No.: US 6,908,883 B2
(45) Date of Patent: Jun. 21, 2005

(54) SYNERGISTICALLY ACTING HERBICIDAL MIXTURES

(75) Inventors: Bernd Sievernich, Böhl-Iggelheim (DE); Max Landes, Gönnheim (DE); Elmar Kibler, Hassloch (DE); Wolfgang von Deyn, Neustadt (DE); Helmut Walter, Obrigheim (DE); Martina Otten, Ludwigshafen (DE); Karl-Otto Westphalen, Speyer (DE); Herve Vantieghem, Stutensee (DE)

(73) Assignee: BASF AG, Ludwigshafen (DE)

( * ) Notice: Subject to any disclaimer, the term of this patent is extended or adjusted under 35 U.S.C. 154(b) by 0 days.

(21) Appl. No.: 10/349,094

(22) Filed: Jan. 23, 2003

(65) Prior Publication Data

US 2003/0203819 A1 Oct. 30, 2003

Related U.S. Application Data

(62) Division of application No. 09/719,429, filed as application No. PCT/EP99/04055 on Jun. 12, 1999, now Pat. No. 6,534,444.

(30) Foreign Application Priority Data

Jun. 16, 1998 (DE) ......................... 198 26 431

(51) Int. Cl.[7] .................... A01N 43/40; A01N 43/56; A01N 43/60; A01N 43/76; A01N 43/80
(52) U.S. Cl. .................... 504/130; 504/136; 504/138; 504/139
(58) Field of Search ................. 504/130, 136, 504/138, 139, 128, 132, 134, 137

(56) References Cited

U.S. PATENT DOCUMENTS

| 5,846,906 A | 12/1998 | von Deyn | 504/221 |
| 5,948,917 A | 9/1999 | Adachi et al. | 548/247 |

FOREIGN PATENT DOCUMENTS

| CA | 2278331 | 7/1998 |
| EP | 900 795 | 3/1999 |
| JP | 2-211610 | 8/1990 |
| WO | 96/26206 | 8/1996 |
| WO | 97/23135 | 7/1997 |
| WO | 97/41116 | 11/1997 |
| WO | 97/41117 | 11/1997 |
| WO | 98/28981 | 7/1998 |
| WO | 98/31681 | 7/1998 |

OTHER PUBLICATIONS

Derwent Abst. 98/28981.
Derwent Abst. 97/23135.
Derwent Abst. 96/211610.

*Primary Examiner*—S. Mark Clardy
(74) *Attorney, Agent, or Firm*—Novak Deuce & Quigg, LLP

(57) ABSTRACT

A synergistic herbicidal mixture comprising
A) at least one benzoyl compound of formula I

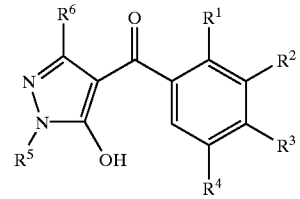

or a salt thereof wherein
$R^1$, $R^3$ are hydrogen, halogen, alkyl, halogenalkyl, alkoxy, halogenalkoxy, alkylthio, alkylsulfinyl or alkylaulfanyl;
$R^2$ is optionally substituted thiazol-2-yl, thiazol-4-yl, thiazol-5-yl, isoxazol-3-yl, isoxazol-4-yl, isoxazol-5-yl, 4,5-dihydroisoxazol-3-yl, 4,5-dihydroisoxazol-4-yl or 4,5-dihydroisoxazol-5-yl;
$R^4$ is hydrogen, halogen or alkyl;
$R^5$ is alkyl;
$R^6$ is hydrogen or alkyl; and
B) a synergistically effective amount of at least one further herbicidal compound as defined in the specification, compositions comprising these mixtures, processes for the preparation of these compositions, and their use for controlling undesired plants.

22 Claims, No Drawings

SYNERGISTICALLY ACTING HERBICIDAL MIXTURES

This is a Divisional application of application Ser. No. 09/719,429, now U.S. Pat. No. 6,534,444 which was filed under Section 371 on Dec. 12, 2000, based on application PCT/EP 99/04055, filed June 12, 1999.

The present invention relates to a synergistic herbicidal mixture comprising

A) at least one 3-heterocyclyl-substituted benzoyl derivative of the formula I

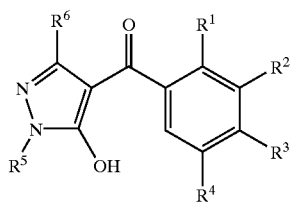

in which the variables have the following meanings:

$R^1$, $R^3$ are hydrogen, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-alkylsulfinyl or $C_1$–$C_6$-alkylsulfonyl;

$R^2$ is a heterocyclic radical selected from the group: thiazol-2-yl, thiazol-4-yl, thiazol-5-yl, isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl, it being possible for the nine radicals mentioned to be unsubstituted or mono- or polysubstituted by halogen, $C_1$–$C_4$-alkyl, $C_1$–$C_4$-alkoxy, $C_1$–$C_4$-haloalkyl, $C_1$–$C_4$-haloalkoxy or $C_1$–$C_4$-alkylthio;

$R^4$ is hydrogen, halogen or $C_1$–$C_6$-alkyl;

$R^5$ is $C_1$–$C_6$-alkyl;

$R^6$ is hydrogen or $C_1$–$C_6$-alkyl;

or one of its environmentally compatible salts;

and

B) a synergistically effective amount of at least one herbicidal compound from the group of the acetyl-CoA carboxylase inhibitors (ACC), acetolactate synthase inhibitors (ALS), amides, auxin herbicides, auxin transport inhibitors, carotenoid biosynthesis inhibitors, enolpyruvylshikimate 3-phosphate synthase inhibitors (ESPS), glutamine synthetase inhibitors, lipid biosynthesis inhibitors, mitosis inhibitors, protoporphyrinogen IX oxidase inhibitors, photosynthesis inhibitors, synergists, growth substances, cell wall biosynthesis inhibitors and a variety of other herbicides.

The invention furthermore relates to herbicidal compositions comprising a herbicidally active amount of a synergistic herbicidal mixture as defined above and at least one liquid and/or solid carrier and, if desired, at least one surfactant.

Moreover, the invention relates to processes for the preparation of these compositions and to a method of controlling undesirable vegetation.

In crop protection products, it is always desirable to increase the specific activity of an active ingredient and the reliability of action. It is an object of the present invention to increase the activity of known, herbicidally active 3-heterocyclyl-substituted benzoyl derivatives of the formula I.

It is an object of the present invention to increase the selective herbicidal activity of the 3-heterocyclyl substituted benzoyl derivatives of the formula I against undesirable harmful plants.

We have found that this object is achieved by the mixtures defined at the outset. We have furthermore found herbicidal compositions which comprise these mixtures, processes for their preparation, and methods of controlling undesirable vegetation. In the last-mentioned cases, it is irrelevant whether the herbicidally active compounds of the components A) and B) are formulated and applied jointly or separately and in which sequence they are applied in the case of separate application.

The mixtures according to the invention show a synergistic effect; the compatibility of the herbicidally active compounds of components A) and B) for certain crop plants is generally retained.

Suitable components B are, as acetyl-CoA carboxylase inhibitors (ACC), for example, cyclohexenone oxime ethers, phenoxyphenoxypropionic esters or arylaminopropionic acids. The acetolactate synthase inhibitors (ALS) include, inter alia, imidazolinones, pyrimidyl ethers, sulfonamides or sulfonyl ureas. Relevant auxin herbicides are, inter alia, pyridine carboxylic acids, 2,4-D or benazolin. Lipid biosynthesis inhibitors which are used are, inter alia, anilides, chloroacetanilides, thioureas, benfuresate or perfluidone. Suitable mitosis inhibitors are, inter alia, carbamates, dinitroanilines, pyridines, butamifos, chlorthal-dimethyl (DCPA) or maleic hydrazide. Examples of protoporphyrinogen IX oxidase inhibitors are, inter alia, diphenyl ethers, oxadiazoles, cyclic imides or pyrazoles. Suitable photosynthesis inhibitors are, inter alia, propanil, pyridate, pyridafol, benzothiadiazinones, dinitrophenols, dipyridylenes, ureas, phenols, chloridazon, triazine, triazinone, uracils or biscarbamates. The synergists are, inter alia, oxiranes. Examples of suitable growth substances are aryloxyalkanoic acids, benzoic acids or quinolinecarboxylic acids. The group "various other herbicides" is to be understood as meaning, inter alia, the classes of the active ingredients dicloropropionic acids, dihydrobenzofurans, phenylacetic acids and individual herbicides mentioned below whose mechanism of action is not (fully) understood.

Other suitable components B are active compounds selected from the group of the amides, auxin transport inhibitors, carotenoic biosynthesis inhibitors, enolpyruvylshikimate 3-phosphate synthase inhibitors (EPSPS), glutamine synthetase inhibitors and cell wall synthesis inhibitors.

Examples of herbicides which can be used in combination with the 3-heterocyclyl-substituted benzoyl derivatives of formula I according to the present invention are, inter alia:

B1 acetyl-CoA carboxylase inhibitors (ACC), for example
cyclohexenone oxime ethers, such as alloxydim, clethodim, cloproxydim, cycloxydim, sethoxydim, tralkoxydim, butroxydim, clefoxydim or tepraloxydim;
phenoxyphenoxypropionic esters, such as clodinafop-propargyl (and, if appropriate, cloquintocet), cyhalofop-butyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl; or arylaminopropionic acids, such as flamprop-methyl or flamprop-isopropyl;

B2 acetolactate synthase inhibitors (ALS), for example imidazolinones, such as imazapyr, imazaquin, imazamethabenz-methyl (imazame), imazamoc, imazapic, imazethapyr or imazamethapyr;

pyrimidyl ethers, such as pyrithiobac-acid, pyrithiobac-sodium, bispyribac-sodium, K1H-6127 or pyribenzoxym;

sulfonamides, such as florasulam, flumetsulam or metosulam; or sulfonylureas, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, N-[[[4-methoxy-6-(trifluoromethyl)-1,3,5-triazin-2-yl]amino]carbonyl]-2-(trifluoromethyl)-benzenesulfonamide, sulfosulfuron or idosulfuron;

B3 amides, for example allidochlor (CDAA), benzoylprop-ethyl, bromobutide, chlorthiamid, diphenamid, etobenzanid (benzchlomet), fluthiamide, fosamin or monalide;

B4 auxin herbicides, for example pyridinecarboxylic acids, such as clopyralid or picloram; or 2,4-D or benazolin;

B5 auxin transport inhibitors, for example naptalame or diflufenzopyr;

B6 carotenoid biosynthesis inhibitors, for example benzofenap, clomazone (dimethazone), diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon or amitrol;

B7 enolpyruvylshikimate-3-phosphate synthase inhibitors (ESPS), for example glyphosate or sulfosate;

B8 glutamine synthetase inhibitors, for example bilanafos (bialaphos) or glufosinate-ammonium;

B9 lipid biosynthesis inhibitors, for example anilides, such as anilofos or mefenacet;

chloroacetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor;

thioureas, such as butylate, cycloate, di-allate, dimepiperate, EPTC, esprocarb, molinate, pebulate, prosulfocarb, thiobencarb (benthiocarb), tri-allate or vernolate; or benfuresate or perfluidone;

B10 mitosis inhibitors, for example carbamates, such as asulam, carbetamid, chlorpropham, orbencarb, pronamid (propyzamid), propham or tiocarbazil;

dinitroanilines, such as benefin, butralin, dinitramin, ethalfluralin, fluchloralin, oryzalin, pendimethalin, prodiamine or trifluralin;

pyridines, such as dithiopyr or thiazopyr; or butamifos, chlorthal-dimethyl (DCPA) or maleic hydrazide;

B11 protoporphyrinogen IX oxidase inhibitors, for example diphenyl ethers, such as acifluorfen, acifluorfen-sodium, aclonifen, bifenox, chlornitrofen (CNP), ethoxyfen, fluorodifen, fluoroglycofen-ethyl, fomesafen, furyloxyfen, lactofen, nitrofen, nitrofluorfen or oxyfluorfen;

oxadiazoles, such as oxadiargyl or oxadiazon;

cyclic imides, such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin; or pyrazoles, such as ET-751, JV 485 or nipyraclofen;

B12 photosynthesis inhibitors, for example propanil, pyridate or pyridafol;

benzothiadiazinones, such as bentazone;

dinitrophenols, for example bromofenoxim, dinoseb, dinoseb-acetate, dinoterb or DNOC;

dipyridylenes, such as cyperquat-chloride, difenzoquat-methylsulfate, diquat or paraquat-dichloride;

ureas, such as chlorbromuron, chlorotoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron;

phenols, such as bromoxynil or ioxynil;

chloridazon;

triazines, such as ametryn, atrazine, cyanazine, desmetryn, dimethamethryn, hexazinone, prometon, prometryn, propazine, simazine, simetryn, terbumeton, terbutryn, terbutylazine or trietazine;

triazinones, such as metamitron or metribuzin;

uracils, such as bromacil, lenacil or terbacil; or biscarbamates, such as desmedipham or phenmedipham;

B13 synergists, for example oxiranes, such as tridiphane;

B14 growth substances, for example aryloxyalkanoic acids, such as 2,4-DB, clomeprop, dichlorprop, dichlorprop-P (2,4-DP-P), fluoroxypyr, MCPA, MCPB, mecoprop, mecoprop-P or triclopyr;

benzoic acids, such as chloramben or dicamba; or quinolinecarboxylic acids, such as quinclorac or quinmerac;

B15 cell wall synthesis inhibitors, for example isoxaben or dichlobenil;

B16 various other herbicides, for example dichloropropionic acids, such as dalapon;

dihydrobenzofurans, such as ethofumesate;

phenylacetic acids, such as chlorfenac (fenac); or aziprotryn, barban, bensulide, benzthiazuron, benzofluor, buminafos, buthidazole, buturon, cafenstrole, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon;
or their environmentally compatible salts.

Of particular importance are the following herbicides which can be used in combination with the 3-heterocyclyl-substituted benzoly [sic] derivatives of the formula I according to the present invention:

B1 acetyl-CoA carboxylase inhibitors (ACC), for example
  cyclohexenone oxime ethers, such as alloxydim, clethodim, cloproxydim, cycloxydim, sethoxydim, tralkoxydim, butroxydim, clefoxydim or tepraloxydim;
  phenoxyphenoxypropionic esters, such as clodinafop-propargyl (and, if appropriate, cloquintocet), cyhalofop-butyl, diclofop-methyl, fenoxaprop-ethyl, fenoxaprop-P-ethyl, fenthiaprop-ethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl; or
  arylaminopropionic acids, such as flamprop-methyl or flamprop-isopropyl;

B2 acetolactate synthase inhibitors (ALS), for example
  imidazolinones, such as imazapyr, imazaquin, imazamethabenz-methyl (imazame), imazapic, imazethapyr or imazamethapyr;
  pyrimidyl ethers, such as pyrithiobac-acid, pyrithiobac-sodium, bispyribac-sodium, K1H-6127 or pyribenzoxym;
  sulfonamides, such as flumetsulam or metosulam; or
  sulfonylureas, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, N-[[[4-methoxy-6-(trifluoromethyl)-1,3,5-triazin-2-yl]amino]carbonyl]-2-(trifluoromethyl)benzenesulfonamide, sulfosulfuron or idosulfuron;

B3 amides, for example
  allidochlor (CDAA), benzoylprop-ethyl, bromobutide, chlorthiamid, diphenamid, etobenzanid (benzchlomet), fluthiamide, fosamine or monalide;

B4 auxin herbicides, for example
  pyridinecarboxylic acids, such as clopyralid or picloram; or
  2,4-D or benazolin;

B5 auxin transport inhibitors, for example
  naptalame or diflufenzopyr;

B6 carotenoid biosynthesis inhibitors, for example
  benzofenap, clomazone (dimethazone), diflufenican, fluorochloridone, fluridone, pyrazolynate, pyrazoxyfen, isoxaflutole, isoxachlortole, mesotrione, sulcotrione (chlormesulone), flurtamone, norflurazon or amitrol;

B7 enolpyruvylshikimate 3-phosphate synthase inhibitors (ESPS), for example
  glyphosate or sulfosate;

B8 glutamine synthetase inhibitors, for example
  bilanafos (bialaphos) or glufosinate-ammonium;

anilides, such as anilofos or mefenacet;
chloracetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor;
thioureas, such as butylate, cycloate, di-allate, dimepiperate, EPTC, esprocarb, molinate, pebulate, prosulfocarb, thiobencarb (benthiocarb), tri-allate or vernolate; or
benfuresate or perfluidone;

B10 mitosis inhibitors, for example
  carbamates, such as asulam, carbetamide, chlorpropham, orbencarb, pronamide (propyzamide), propham or thiocarbazil;
  dinitroanilines, such as benefin, butralin, dinitramine, ethalfluralin, fluchloralin, oryzalin, pendimethalin, prodiamine or trifluralin;
  pyridines, such as dithiopyr or thiazopyr; or
  butamifos, chlorthal-dimethyl (DCPA) or maleic hydrazide;

B11 protoporphyrinogen IX oxidase inhibitors, for example
  diphenyl ethers, such as acifluorfen, acifluorfen-sodium, aclonifen, bifenox, chlornitrofen (CNP), ethoxyfen, fluorodifen, fluoroglycofen-ethyl, fomesafen, furyloxyfen, lactofen, nitrofen, nitrofluorfen or oxyfluorfen;
  oxadiazoles, such as oxadiargyl or oxadiazon;
  cyclic imides, such as azafenidin, carfentrazone-ethyl, cinidon-ethyl, flumiclorac-pentyl, flumioxazin, flumipropyn, flupropacil, fluthiacet-methyl, sulfentrazone or thidiazimin; or
  pyrazoles, such as ET-751, JV 485 or nipyraclofen;

B12 photosynthesis inhibitors, for example
  propanil, pyridate;
  benzothiadiazinones, such as bentazon;
  dinitrophenols, such as bromofenoxim, dinoseb, dinoseb-acetate, dinoterb or DNOC;
  dipyridylenes, such as cyperquat-chloride, difenzoquat-methylsulfate, diquat or paraquat-dichloride;
  ureas, such as chlorbromuron, chlorotoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron;
  phenols, such as bromoxynil or ioxynil;
  chloridazon;
  triazines, such as ametryn, atrazine, cyanazine, desmetryn, dimethamethryn, hexazinone, prometon, prometryn, propazin, simazine, simetryn, terbumeton, terbutryn, terbutylazine or trietazine;
  triazinones, such as metamitron or metribuzin;
  uracils, such as bromacil, lenacil or terbacil; or
  biscarbamates, such as desmedipham or phenmedipham;

B13 synergists, for example
  oxiranes, such as tridiphane;

B14 growth substances, for example
  aryloxyalkanoic acids, such as 2,4-DB, clomeprop, dichlorprop, dichlorprop-P (2,4-DP-P), fluoroxypyr, MCPA, MCPB, mecoprop, mecoprop-P or triclopyr;
  benzoic acids, such as chloramben or dicamba; or quinolinecarboxylic acids, such as quinclorac or quinmerac;

B15 cell wall synthesis inhibitors, for example isoxaben or dichlobenil;

B16 various other herbicides, for example dichloropropionic acids, such as dalapon; dihydrobenzofurans, such as ethofumesate; phenylacetic acids, such as chlorfenac (fenac); or aziprotryn, barban, bensulide, benzthiazuron, benzofluor, buminafos, buthidazole, buturon, cafenstrole, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triazofenamid or trimeturon;

or their environmentally compatible salts.

The 3-heterocyclyl-substituted benzoyl derivatives of the formula I are disclosed in WO 96/26206, WO 97/41116, WO 97/41117 and WO 97/41118.

They can exist, or be used, in the form of the pure enantiomers and also as racemates or diastereomer mixtures. The 3-heterocyclyl-substituted benzoyl derivatives of the formula I and the herbicidally active compounds from amongst groups B1 to B16 may also exist in the form of their environmentally compatible salts. Suitable salts are, in general, the salts of those cations, or the acid addition salts of those acids, whose cations, or anions, respectively, do not adversely affect the herbicidal action of the active ingredients.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, it being possible in this case, if desired, for one to four hydrogen atoms to be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-yl ammonium, di(2-hydroxyeth-1-yl)ammonium, trimethylbenzylammonium, furthermore phosphonium ions, sulfonium ions, preferably tri($C_1$–$C_4$-alkyl)sulfonium and sulfoxonium ions, preferably, tri($C_1$–$C_4$-alkyl)sulfoxonium.

Anions of suitable acid addition salts are mainly chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, propionate and butyrate.

The herbicidally active compounds from amongst groups B1 to B16 are described, for example, in "Herbizide [Herbicides]", Hock, Fedtke, Schmidt, 1st edition, Thieme 1995 (s. "quinclorac" p. 238, "molinat" p. 32, "butachlor" p. 32, "pretilachlor" p. 32, "dithiopyr" p. 32, "mefenacet" p. 32, "fenoxapropethyl" p. 216, "dimepiperate" p. 32, "pyrazolynate" p. 146, "pyrazoxyfen" p. 146, "bensulfuronmethyl" p. 31, "pyrazosulfuron-ethyl" p. 31, "cinosulfuron" p. 31, "benfuresate" p. 233, "bromobutide" p. 243, "dymron" p. 243, "dimethyametryn" p. 118, "esprocarb" p. 229, "pyributicarb" p. 32, "cinemthylin" p. 32, "propanil" p. 32, "2,4-D" p. 30, "bentazon" p. 30, "azimsulfuron (DPX-A-8947)" p. 175, "mecoprop-P" p. 237, "chlorpropham" p. 205, "ethoxyfen" p. 30, "haloxyfop-P-methyl" p. 38, "haloxyfop-ethoxyethyl" p. 38, "flumiclorac-pentyl" p. 35, "flupropacil" p. 143, "nipyraclofen" p. 145, "metosulam" p. 33, "ethametsulfuron-methyl" p. 36, "thifensulfuron-methyl" p. 35, "pyrithiobac acid" p. 181);

"Agricultural Chemicals", Book II Herbicides, 1993 (s. "thiobencarb" p. 85, "benzofenap" p. 221, "napropanilid" p. 49, "piperophos" p. 102, "anilofos" p. 241, "imazosulfuron (TH-913)" p. 150, "etobenzamid (HW-52)" p. 54, "sulcotrione (ICIA-0051)" p. 268, "poast" p. 253, "focus" p. 222, 45 "dimethenamid" p. 48, "sulfosate" p. 236, "12,4-DB" p. 10, "dichlorprop-P" p. 6, "flupoxam" p. 44, "prosulfocarb" p. 84, "quinmerac" p. 233, "metazachlor" p. 64, "flurtamone" p. 265, "bromofenoxim" p. 228, "fomesafen" p. 248, "imazamethabenz-methyl" p. 153, "clodinafop-propargyl" p. 214, "fenoxaprop-P-ethyl" p. 208, "fluazifop-P-butyl" p. 207, "quizalofop-P-ethyl" p. 210, "quizalofop-terfuryl" p. 211, "flumioxazin" p. 43, "flumipropyn" p. 267, "sulfentrazone" p. 261, "thiazopyr" p. 226, "pyrithiobac-sodium" p. 266, "flumetsulam" p. 227, "amidosulfuron" p. 151, "halosulfuron-methyl" p. 148, "rimsulfuron" p. 138, "tribenuron-methyl" p. 139, "triflusulfuron-methyl" p. 137, "primisulfuron-methyl" p. 147);

"Agricultural Chemicals", Book II Herbicides, 13$^{th}$ Edition (s. "carfenstole" p. 284, "sulfosulfuron" p. 145, "ethoxysulfuron" p. 149, "pyribenzoxym" p. 279, "diflufenzopyr" p. 90, "ET-751" p. 278, "carfentrazone-ethyl" p. 267, "fluthiacet-methyl" p. 277, "imazapic" p. 160, "butenachlor" p. 54, "tiocarbazil" p. 84, "fluthiamide" p. 62, "isoxaflutole" p. 283, "butroxydim" p. 259,)

"Short Review of Herbicides & PGRs 1991, Hodogaya Chemicals (s. "furyloxyfen" p. 142, "triazofenamid" p. 268, "thenylchlorid (NSK-850)" p. 52, "cumyluron (JC-940)" p. 90, "pendimethalin (AC-92553)" p. 58, "buthidazole" p. 88, "cyprazole" p. 38, "allidochlor" p. 48, "benzoylprop-ethyl" p. 38, "chlorthiamid" p. 150, "diphenamid" p. 34, "flamprop-methyl" p. 40, "fosamin" p. 232, "isoxaben" p. 42, "monalide" p. 32, "naptalam" p. 36, "pronamid" p. 34, "bialaphos" p. 234, "glufosinate-ammonium" p. 234, "glyphosate" p. 232, "amitrol" p. 254, "clomeprop p. 20, "dichlorprop" p. 6, "fenoprop" p. 8, "fluroxypyr" p. 156, "MCPA" p. 4, "MCPB" p. 8, "mecoprop" p. 6, "napropamide" p. 16, "triclopyr" p. 154, "chloramben" p. 28, "dicamba" p. 26, , "clomazone" p. 268, "diflufenican" p. 42, "fluorochloridone" p. 266, "fluridone" p. 156, "asulalm" p. 112, "barban" p. 100, "butylate" p. 106, "carbetamide" p. 36, "chlorbufam" p. 100, "cycloate" p. 108, "desmedipham" p. 104, "di-allate" p. 106, "EPTC" p. 108, "orbencarb" p. 112, "pebulate" p. 106, "phenisopham" p. 118, "phenmedipham" p. 104, "propham" p. 100, "sulfallate" p. 110, "terbucarb" p. 102, "tri-allate" p. 108, "vernolate" p. 108, "acetochlor" p. 48, "alachlor" p. 46, "diethathyl-ethyl" p. 48, "dimethachlor" p. 50, "metolachlor" p. 46, "propachlor" p. 44, "pyrnachlor" p. 44, "terbuchlor" p. 48, "xylachlor" p. 52, "alloxydim" p. 260, "clethodim" p. 270, "cloproxydim" p. 268, "tralkoxydim" p. 270, "dalapon" p. 212, "ethofumesate" p. 124, "benefin" p. 54, "butralin" p. 58, "dinitramin" p. 56, "ethalfluralin" p. 60, "fluchloralin" p. 54, "isopropalin" p. 58, "nitralin" p. 58, "oryzalin" p. 60, "prodiamine" p. 62, "profluralin" p. 54, "trifluralin" p. 54, "dinoseb" p. 128, "dinoseb-acetate" p. 128, "dinoterb" p. 128, "DNOC" p. 126, "acifluorfen-sodiumn" p. 142, "aclonifen" p. 146, "bifenox" p. 140, "chlornitrofen" p. 138, "difenoxuron" p. 76, "fluorodifen" p. 138, "fluoroglycofen-ethyl" p. 146, "lactofen" p. 144, "nitrofen" p. 136, "nitrofluorfen" p. 140, "oxyfluorfen" p. 140, "cyperquat-chloride" p. 158, "difenzoquat-methylsulfate" p. 160, "diquat" p. 158, "paraquat-dichloride" p. 158, "benzthiazuron" p. 82, "buturon" p. 66, "chlorbromuron" p. 72, "chloroxuron" p. 76, "chlorotoluron" p. 74, "cycluron" p. 84, "dimefuron" p. 88, "diuron" p. 70, "lethidimuron" p. 86, "fenuron" p. 64, "fluometuron" p. 68, "isoproturon" p. 80, "isouron" p. 88, "karbutilate" p. 76, "linuron" p. 72, "methabenzthiazuron" p. 82, "metoxuron" p. 72, "monolinuron" p. 66, "rmonuron" p. 64, "neburon" p. 72, "siduron" p. 68, "tebuthiuron" p. 86, "trimeturon" p. 64, "isocarbamid" p. 168, "iimazamethapyr" p. 172, "imazapyr" p. 170, "iimazaquin" p. 170, "iimazethapyr" p. 172, "methazole" p. 162, "oxadiazon" p. 162, "tridiphane" p. 266, "bromoxynil" p. 148, "ioxynil" p. 148, "diclofop-methyl" p. 16, "fenthiaprop-ethyl" p. 20, "fluazifop-butyl" p. 18, "haloxyfop-methyl" p. 18, "isoxapyrifop" p. 22, "propaquizafop" p. 24, "quizalofop-ethyl" p. 20, "chlorfenac" p. 258, "chlorfenprop-methyl" p. 258, "chloridazon" p. 174, "maleic hydrazide" p. 162, "norflurazon" p. 174, "pyridate" p. 176, "clopyralid" p. 154, "picloramr" p. 154, "chlorimuron-ethyl" p. 92, "chlorsulfuron" p. 92, "flazasulfuron" p. 96, "metsulfuron-methyl" S.92, "nicosulfuron" p. 96, "sulfometuron-methyl" p. 92, "triasulfuron" p. 94, "ametryn" p. 198, "atrazine" p. 188, "aziprotryne" p. 206, "cyanazine" p. 192, "cyprazine" p. 192, "desmetryne" p. 200, "dipropetryn" p. 202, "eglinazine-ethyl" p. 208, "hexazinone" p. 208, "procyazine" p. 192, "prometone" p. 196, "prometryn" p. 196, "propazine" p. 188, "secbumeton" p. 196, "simazine" p. 188, "simetryn" p. 196, "terbumeton" p. 204, "terbutryn" p. 198, "terbutylazine" p. 190, "trietazine" p. 188, "lethiozine" p. 210, "metamitron" p. 206, "metribuzin" p. 202, "bromacil" p. 180, "lenacil" p. 180, "terbacil" p. 180, "benazolin" p. 262, "bensulide" p. 228, "benzofluor" p. 266, "butamifos" p. 228, "DCPA" p. 28, "dichlobenil", p. 148, "endothal" p. 264, "rmefluidide" p. 306, "perfluidone" p. 260, "terbuchlor" p. 48);

"Global Herbicide Directory" First Edition, 1994 (s. "oxadiargyl" p. 96);

"European Directory of Agrochemical Products" Volume 2-Herbicides" Fourth Edition, (s. "buminafos" p. 255).

Moreover, the compound "DEH-112" is disclosed in European Patent Application EP-A 302 203. The compound "tepraloxydim" is described in DE-A 33 36 140; the compound "cinidon-ethyl" in DE-A 36 03 789 and the compound "fluorbentranil" in EP-A 84 893. Other compounds are known from "Brighton Crop Protection Conference—Weeds—1993 (S. "thidiazimin" p. 29, "AC-322140" p. 41, "K1H-6127" p. 47, "prosulfuron" p. 53, "K1H-2023" p. 61, "metobenzuron" p. 67). The compound "carfenstrole (CH-900)" is mentioned in EP-A 332 133, and the compound N-[[[4-methoxy-6-(trifluoromethyl)-1,3,5-triazin-2-yl]amino]-carbonyl]-2-(trifluoromethylbenzenesulfonamide) is described in PCT/EP 96/03996.

The assignment of the active ingredients to the respective mechanisms of action is based on current knowledge. If several mechanisms of action apply to one active ingredient, this substance was only assigned to one mode of action.

Preferred with regard to the synergistic herbicidal action of the mixtures according to the invention are those 3-heterocyclyl-substituted benzoyl derivatives of the formula I in which the variables have the following meanings, either alone or in combination:

$R^1$ halogen, $C_1$–$C_6$-alkyl, $C_1$–$C_6$-alkylthio, $C_1$–$C_6$-alkylsulfinyl or $C_1$–$C_6$-alkylsulfonyl;

especially preferably halogen, such as chlorine or bromine, $C_1$–$C_6$-alkyl, such as methyl or ethyl, or $C_1$–$C_6$-alkylsulfonyl, such as methylsulfonyl or ethylsulfonyl;

very particularly preferably chlorine, methyl or methylsulfonyl;

$R^2$ a heterocyclic radical selected from the group: isoxazol-3-yl, isoxazol-5-yl and 4,5-dihydroisoxazol-3-yl, it being possible for the three radicals mentioned to be unsubstituted or mono- or polysubstituted by halogen, $C_1$–$C_4$-alkyl, $C_1$–$C_4$-alkoxy, $C_1$–$C_4$-haloalkyl, $C_1$–$C_4$-haloalkoxy or $C_1$–$C_4$-alkylthio;

especially preferably isoxazol-5-yl, 3-methyl-isoxazol-5-yl, 4,5-dihydroisoxazol-3-yl, 5-methyl-4,5-dihydroisoxazol-yl, 5-ethyl-4,5-dihydroisoxazol-3-yl or 4,5-dimethyl-4,5-dihydroisoxazol-3-yl; also preferred is a heterocyclic radical selected from the group: thiazol-2-yl, thiazol-4-yl, thiazol-5-yl, isoxazol-4-yl, 4,5-dihydroisoxazol-4-yl and 4,5-dihydroisoxazol-5-yl, it being possible for the six radicals mentioned to be unsubstituted or mono- or polysubstituted by halogen, $C_1$–$C_4$-alkyl, $C_1$–$C_4$-alkoxy, $C_1$–$C_4$-haloalkyl, $C_1$–$C_4$-haloalkoxy or $C_1$–$C_4$-alkylthio;

$R^3$ halogen, $C_1$–$C_6$-alkyl, $C_1$–$C_6$-alkylthio, $C_1$–$C_6$-alkylsulfinyl or $C_1$–$C_6$-alkylsulfonyl;

especially preferably halogen, such as chlorine or bromine, $C_1$–$C_6$-alkylthio, such as methylthio or ethylthio, $C_1$–$C_6$-alkylsulfinyl, such as methylsulfinyl or ethylsulfinyl, or $C_1$–$C_6$-alkylsulfonyl, such as methylsulfonyl or ethylsulfonyl;

very particularly preferably chlorine, methylsulfonyl or ethylsulfonyl;

$R^4$ hydrogen or methyl; especially preferably hydrogen;

$R^5$ is $C_1$–$C_6$-alkyl, such as methyl, ethyl, propyl, 1-methylethyl, butyl, 1-methylpropyl or 2-methylpropyl; especially preferably methyl, ethyl or 1-methylethyl;

$R^6$ hydrogen or $C_1$–$C_6$ alkyl, such as methyl or ethyl; especially preferably hydrogen or methyl.

Very particularly preferred are those 3-heterocyclyl-substituted benzoyl derivatives of the formula Ia, in particular the compounds Ia.1 to Ia.53, which are mentioned in Table 1 which follows:

TABLE 1

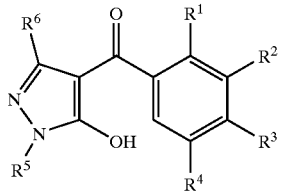

Ia

| No. | $R^1$ | $R^2$ | $R^3$ | $R^4$ | $R^5$ | $R^6$ |
|---|---|---|---|---|---|---|
| Ia.1 | Cl | 4,5-dihydroisoxazol-3-yl | $SO_2CH_3$ | H | $CH_3$ | $CH_3$ |
| Ia.2 | Cl | 4,5-dihydroisoxazol-3-yl | Cl | H | $CH_3$ | $CH_3$ |
| Ia.3 | Cl | 4,5-dihydroisoxazol-3-yl | $SO_2CH_3$ | H | $CH_3$ | H |
| Ia.4 | Cl | 4,5-dihydro-5-methylisoxazol-3-yl | $SO_2CH_3$ | H | $CH_3$ | H |
| Ia.5 | Cl | 4,5-dihydro-5,5-dimethylisoxazol-3-yl | $SO_2CH_3$ | H | $CH_3$ | H |
| Ia.6 | Cl | 4,5-dihydro-5-ethylisoxazol-3-yl | $SO_2CH_3$ | H | $CH_3$ | H |
| Ia.7 | Cl | 4,5-dihydro-5,5-diethylisoxazol-3-yl | $SO_2CH_3$ | H | $CH_3$ | H |
| Ia.8 | Cl | 4,5-dihydro-5-chloromethylisoxazol-3-yl | $SO_2CH_3$ | H | $CH_3$ | H |
| Ia.9 | Cl | 4,5-dihydroisoxazol-3-yl | $SCH_3$ | H | $CH_3$ | H |
| Ia.10 | Cl | 4,5-dihydro-5-ethoxyisoxazol-3-yl | $SO_2CH_3$ | H | $CH_3$ | H |
| Ia.11 | Cl | 4,5-dihydro-5-methoxyisoxazol-3-yl | $SO_2CH_3$ | H | $CH_3$ | H |
| Ia.12 | Cl | 4,5-dihydro-4,5-dimethylisoxazol-3-yl | $SO_2CH_3$ | H | $CH_3$ | H |
| Ia.13 | Cl | 4,5-dihydro-5-thioethylisoxazol-3-yl | $SO_2CH_3$ | H | $CH_3$ | H |
| Ia.14 | Cl | 4,5-dihydro-5-trifluoromethylisoxazol-3-yl | $SO_2CH_3$ | H | $CH_3$ | H |
| Ia.15 | $SCH_3$ | 4,5-dihydroisoxazol-3-yl | $SCH_3$ | H | $CH_3$ | H |
| Ia.16 | Cl | 4,5-dihydroisoxazol-3-yl | $SO_2CH_3$ | H | $C_2H_5$ | H |
| Ia.17 | Cl | 4,5-dihydroisoxazol-3-yl | Cl | H | $C_2H_5$ | H |
| Ia.18 | Cl | 4,5-dihydro-5-methylisoxazol-3-yl | $SO_2CH_3$ | H | $C_2H_5$ | H |
| Ia.19 | Cl | 4,5-dihydro-5,5-dimethylisoxazol-3-yl | $SO_2CH_3$ | H | $C_2H_5$ | H |
| Ia.20 | Cl | 4,5-dihydro-5-ethylisoxazol-3-yl | $SO_2CH_3$ | H | $C_2H_5$ | H |
| Ia.21 | Cl | 4,5-dihydro-5,5-diethylisoxazol-3-yl | $SO_2CH_3$ | H | $C_2H_5$ | H |
| Ia.22 | Cl | 4,5-dihydroisoxazol-3-yl | $SCH_3$ | H | $C_2H_5$ | H |
| Ia.23 | Cl | 4,5-dihydro-5-chloromethylisoxazol-3-yl | $SO_2CH_3$ | H | $C_2H_5$ | H |
| Ia.24 | Cl | 4,5-dihydroisoxazol-3-yl | $SOCH_3$ | H | $C_2H_5$ | H |
| Ia.25 | Cl | 4,5-dihydro-5-ethoxyisoxazol-3-yl | $SO_2CH_3$ | H | $C_2H_5$ | H |
| Ia.26 | Cl | 4,5-dihydro-4,5-dimethylisoxazol-3-yl | $SO_2CH_3$ | H | $C_2H_5$ | H |
| Ia.27 | Cl | 4,5-dihydro-5-thioethylisoxazol-3-yl | $SO_2CH_3$ | H | $C_2H_5$ | H |
| Ia.28 | Cl | 4,5-dihydro-5-trifluoromethylisoxazol-3-yl | $SO_2CH_3$ | H | $C_2H_5$ | H |
| Ia.29 | $SCH_3$ | 4,5-dihydroisoxazol-3-yl | $SCH_3$ | H | $C_2H_5$ | H |
| Ia.30 | Cl | 4,5-dihydroisoxazol-3-yl | $SO_2CH_3$ | H | $i-C_4H_9$ | H |
| Ia.31 | $CH_3$ | 4,5-dihydroisoxazol-3-yl | $SO_2CH_3$ | H | $CH_3$ | $CH_3$ |
| Ia.32 | $CH_3$ | 4,5-dihydroisoxazol-3-yl | Cl | H | $CH_3$ | $CH_3$ |
| Ia.33 | $CH_3$ | 4,5-dihydroisoxazol-3-yl | $SO_2CH_3$ | H | $CH_3$ | H |
| Ia.34 | $CH_3$ | 4,5-dihydro-5-methylisoxazol-3-yl | $SO_2CH_3$ | H | $CH_3$ | H |
| Ia.35 | $CH_3$ | 4,5-dihydro-5,5-dimethylisoxazol-3-yl | $SO_2CH_3$ | H | $CH_3$ | H |
| Ia.36 | $CH_3$ | 4,5-dihydro-5-ethylisoxazol-3-yl | $SO_2CH_3$ | H | $CH_3$ | H |
| Ia.37 | $CH_3$ | 4,5-dihydro-5,5-diethylisoxazol-3-yl | $SO_2CH_3$ | H | $CH_3$ | H |
| Ia.38 | $CH_3$ | 4,5-dihydroisoxazol-3-yl | $SO_2CH_3$ | H | $CH_3$ | H |
| Ia.39 | $CH_3$ | 4,5-dihydro-4,5-dimethylisoxazol-3-yl | $SO_2CH_3$ | H | $CH_3$ | H |
| Ia.40 | $CH_3$ | 4,5-dihydroisoxazol-3-yl | $SO_2CH_3$ | H | $C_2H_5$ | H |
| Ia.41 | $CH_3$ | 4,5-dihydroisoxazol-3-yl | Cl | H | $C_2H_5$ | H |
| Ia.42 | $CH_3$ | 4,5-dihydro-5-methylisoxazol-3-yl | $SO_2CH_3$ | H | $C_2H_5$ | H |
| Ia.43 | $CH_3$ | 4,5-dihydro-5,5-dimethylisoxazol-3-yl | $SO_2CH_3$ | H | $C_2H_5$ | H |
| Ia.44 | $CH_3$ | 4,5-dihydro-5-ethylisoxazol-3-yl | $SO_2CH_3$ | H | $C_2H_5$ | H |
| Ia.45 | $CH_3$ | 4,5-dihydro-5-diethylisoxazol-3-yl | $SO_2CH_3$ | H | $C_2H_5$ | H |
| Ia.46 | $CH_3$ | 4,5-dihydro-4,5-dimethylisoxazol-3-yl | $SO_2CH_3$ | H | $C_2H_5$ | H |
| Ia.47 | $CH_3$ | 4,5-dihydroisoxazol-3-yl | $SO_2CH_3$ | H | $i-C_4H_9$ | H |
| Ia.48 | Cl | 2-thiazolyl | $SO_2CH_3$ | H | $CH_3$ | $CH_3$ |
| Ia.49 | Cl | 2-thiazolyl | $SO_2CH_3$ | H | $CH_3$ | H |
| Ia.50 | Cl | 2-thiazolyl | $SO_2CH_3$ | H | $C_2H_5$ | H |
| Ia.51 | $CH_3$ | 2-thiazolyl | $SO_2CH_3$ | H | $CH_3$ | $CH_3$ |
| Ia.52 | Cl | 3-methylisoxazol-5-yl | $SO_2CH_3$ | H | $CH_3$ | H |
| Ia.53 | Cl | 3-methylisoxazol-5-yl | $SO_2CH_3$ | H | $C_2H_5$ | H |

Also very particularly preferred are the compounds Ib, in particular the compounds Ib.1 to Ib.53, which differ from the compounds Ia.1 to Ia.53 only by the fact that they are present as the sodium salt:

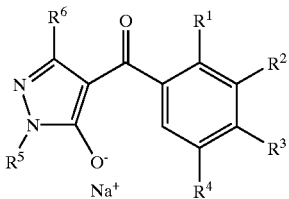

Ib

Also very particularly preferred are the compounds Ic, in particular the compounds Ic.1 to Ic.53, which differ from the compounds Ia.1 to Ia.53 only by the fact that they are present as the lithium salt:

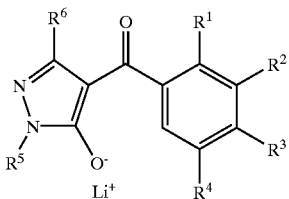

Ic

Also very particularly preferred are the compounds Id, in particular the compounds Id.1 to Id.53, which differ from the compounds Ia.1 to Ia.53 only by the fact that they are present as the potassium salt:

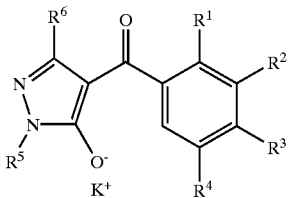

Id

Also very particularly preferred are the compounds Ie, in particular the compounds Ie.1 to Ie.53, which differ from the compounds Ia.1 to Ia.53 only by the fact that they are present as the ammonium salt:

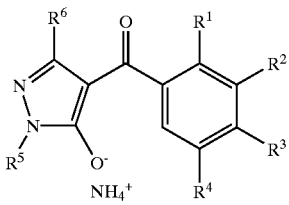

Ie

Very particularly preferred are, especially, the compounds Ia, especially the compounds Ia.1 to Ia.53.

Very particularly preferred are, moreover, the 3-heterocyclyl substituted benzoyl derivatives of the formula I where $R^2$ is a heterocyclic radical selected from amongst the group: thiazol-2-yl, thiazol-4-yl and thiazol-5-yl, it being possible for the three radicals mentioned to be unsubstituted or mono- or polysubstituted by halogen, $C_1-C_4$-alkyl, $C_1-C_4$-alkoxy, $c_1-C_4$-haloalkyl, $c_1-C_4$-haloalkoxy or $C_1-C_4$-alkylthio.

Very particularly preferred are, especially, the 3-heterocyclyl-substituted benzoyl derivatives of the formula I, where $R^4$ is hydrogen.

Very particularly preferred are, moreover, the 3-heterocyclyl substituted benzoyl derivatives of the formula I where $R^2$ is a heterocyclic radical selected from the group: isoxazol-3-yl, isoxazol-4-yl and isoxazol-5-yl, it being possible for the three radicals mentioned to be unsubstituted or mono- or polysubstituted by halogen, $C_1-C_4$-alkyl, $C_1-C_4$-alkoxy, $C_1-C_4$-haloalkyl, $C_1-C_4$-haloalkoxy or $C_1-C_4$-alkylthio.

Very particularly preferred are, especially, the 3-heterocyclyl-substituted benzoyl derivatives of the formula I, where $R^2$ is isoxazol-3-yl which can be unsubstituted or mono- or polysubstituted by halogen, $C_1-C_4$-alkyl, $C_1-C_4$-alkoxy, $C_1-C_4$-haloalkyl, $C_1-C_4$-haloalkoxy or $C_1-C_4$-alkylthio.

$R^4$ is hydrogen.

Very especially preferred are also in particular the 3-heterocyclyl-substituted benzoyl derivatives of the formula I where $R^2$ is isoxazol-5-yl, which can be unsubstituted or mono- or polysubstituted by halogen, $C_1-C_4$-alkyl, $C_1-C_4$-alkoxy, $C_1-C_4$-haloalkyl, $C_1-C_4$-haloalkoxy or $C_1-C_4$-alkylthio;

$R^4$ is hydrogen.

Most particularly preferred is
4-[2-chloro-3-(3-methyl-isoxazol-5-yl)-4-methylsulfonyl-benzoyl]-1-methyl-5-hydroxy-1H-pyrazole.

Very particularly preferred are, moreover, the 3-heterocyclyl-substituted benzoyl derivatives of the formula I where $R^2$ is a heterocyclic radical selected from the group: 4,5-dihydroisoxazol-3-yl, 4,5-dihydroisoxazol-4-yl and 4,5-dihydroisoxazol-5-yl, it being possible for the three radicals mentioned to be unsubstituted or mono- or polysubstituted by halogen, $C_1-C_4$-alkyl, $C_1-C_4$-alkoxy, $C_1-C_4$-haloalkyl, $C_1-C_4$-haloalkoxy or $C_1-C_4$-alkylthio.

Very particularly preferred are, especially, the 3-heterocyclyl-substituted benzoyl derivatives of the formula I where $R^2$ is 4,5-dihydroisoxazol-3-yl which can be unsubstituted or mono- or polysubstituted by halogen, $C_1-C_4$-alkyl, $C_1-C_4$-alkoxy, $C_1-C_4$-haloalkyl, $C_1-C_4$-haloalkoxy, or $C_1-C_4$-alkylthio; and $R^4$ is hydrogen.

Most particularly preferred are the 3-heterocyclyl-substituted benzoyl derivatives of the formula I where $R^1$ is halogen or $C_1-C_6$-alkyl; and
$R^3$ is $C_1-C_6$-alkylsulfonyl.

Most especially preferred is 4-[2-chloro-3-(4,5-dihydroisoxazol-3-yl)-4-methylsulfonyl-benzoyl)-1-methyl-5-hydroxy-1H-pyrazole.

Most particularly preferred is also 4-[2-methyl-3-(4,5-dihydroisoxazol-3-yl)-4-methylsulfonyl-benzoyl]-1-methyl-5-hydroxy-1H-pyrazole.

With a view to the synergistic herbicidal action of the mixtures according to the invention, compounds from amongst groups B1 to B14 or B16, preferably from amongst groups B1 to B14, are preferred as component B).

In particular, compounds from amongst the classes of active ingredients mentioned below are preferred, or the following compounds are very particularly preferred:

B1 acetyl-CoA carboxylase inhibitors (ACC):
  cyclohexenone oxime ethers, in particular cycloxydim, sethoxydim or tralkoxydim, preferably sethoxydim or tralkoxydim; or
  phenoxyphenoxypropionic esters, in particular clodinafop-propargyl (and, if appropriate, cloquintocet), fenoxaprop-ethyl or fenoxaprop-P-ethyl, preferably clodinafop-propargyl (and, if appropriate, cloquintocet) or fenoxaprop-p-ethyl (sic];

B2 acetolactate synthase inhibitors (ALS):
  imidazolinones, in particular imazapyr, imazaquin, imazamethabenz, imazethapyr or imazamoc, preferably imazapyr;
  pyrimidyl ethers, in particular pyrithiobac sodium;
  sulfonamides, in particular florasulam, flumetsulam or metosulam, preferably metosulam; or
  sulfonylureas, in particular halosulfuron-methyl, nicosulfuron, primisulfuron-methyl, prosulfuron, rimsulfuron, thifensulfuron-methyl, tribenuron-methyl, N-[[[4-methoxy-6-(trifluoromethyl)-1,3,5-triazin-2-yl]-amino]carbonyl]-2-(trifluoromethyl)-benzenesulfonamide or sulfosulfuron;

B3 amides:
  fluthiamide;

B4 auxin herbicides:
  pyridinecarboxylic acids, in particular clopyralid; or 2,4-D;

B5 auxin transport inhibitors:
  diflufenzopyr;

B6 carotenoid biosynthesis inhibitors:
  isoxaflutole, mesotrione, isoxachloride, ketospiradox or sulcotrione (chlormesulone), in particular isoxaflutole or sulcotrione;

B7 enolpyruvylshikimate-3-phosphate synthase inhibitors (ESPS):
  glyphosate or sulfosate;

B8 glutamin synthetase inhibitors:
  glufosinate-ammonium;

B9 lipid biosynthesis inhibitors:
  chloroacetanilides, in particular dimethenamid, S-dimethenamid, acetochlor, metolachlor or S-metolachlor,
  thioureas, in particular benthiocarb;

B10 mitosis inhibitors:
  dinitroanilines, in particular pendimethalin;

B11 protoporphyrinogen IX oxidase inhibitors:
  diphenyl ethers, in particular acifluorfen or acifluorfen-sodium;
  oxadiazoles, in particular oxadiargyl; or
  cyclic imides, in particular butafenacil, carfentrazone-ethyl, cinidon-ethyl or flumiclorac-pentyl, preferably carfentrazone-ethyl, cinidon-ethyl or flumidorac-pentyl;
  pyrazoles, in particular JV 485;

B12 photosynthesis inhibitors:
  pyridate or pyridafol, in particular pyridate;
  benzothiadiazinones, in particular bentazone;
  dipyridylenes, in particular paraquat-dichloride;
  ureas, in particular diuron or isoproturon, preferably diuron;
  phenols, in particular bromoxynil;
  chloridazone;
  triazines, in particular atrazine or terbutylazine; or
  triazinones, in particular metribuzin;

B13 synergists:
  oxiranes, in particular tridiphane;

B14 growth substances:
  aryloxyalkanoic acids, in particular fluoroxypyr, MCPA or mecoprop-P;
  benzoic acids, in particular dicamba; or
  quinolinecarboxylic acids, in particular quinclorac;

B16 various other herbicides:
  triaziflam.

Also preferred as component B) are compounds from amongst the groups B1, B2, B4 to B12 and B14.

In particular, compounds from amongst the classes of active ingredients mentioned below are preferred, or the following compounds are very particularly preferred:

B1 acetyl-CoA carboxylase inhibitors (ACC):
  cyclohexenone oxime ethers, in particular cycloxydim or sethoxydim;
  phenoxyphenoxypropionic esters, in particular clodinafop-propargyl (and, if appropriate, cloquintocet), fenoxaprop-ethyl or fenoxaprop-P-ethyl, preferably clodinafop-propargyl (and, if appropriate, cloquintocet);

B2 acetolactate synthase inhibitors (ALS):
  imidazolinones, in particular imazapyr, imazaquin, imazamethabenz or imazethapyr, preferably imazapyr;
  pyrimidyl ethers, in particular pyrithiobac-sodium;
  sulfonamides, in particular flumetsulam or metosulam, preferably metosulam; or
  sulfonylureas, in particular halosulfuron-methyl, nicosulfuron or N-[[[4-methoxy-6-(trifluoromethyl)-1,3,5-triazin-2-yl]amino]carbonyl]-2-(trifluoromethyl)-benzenesulfonamide, preferably nicosulfuron or N-[[[4-methoxy-6-(trifluoromethyl)-1,3,5-triazin-2-yl]-amino]carbonyl]-2-(trifluoromethyl)-benzenesulfonamide;

B4 auxin herbicides:
  2,4-D;

B5 auxin transport inhibitors:
  diflufenzopyr;

B6 carotenoid biosynthesis inhibitors:
  isoxaflutole or sulcotrione, preferably isoxaflutole;

B7 enolpyruvylshikimat-3-phosphate synthase inhibitors (ESPS):
  glyphosate;

B8 glutamine synthetase inhibitors:
  glufosinate-ammonium;

B9 lipid biosynthesis inhibitors:
  chloracetanilide, in particular dimethenamid, S-dimethenamid, acetochlor, metolachlor or S-metolachlor;
  thioureas, in particular benthiocarb;

B10 mitosis inhibitors:
  dinitroaniline, in particular pendimethalin;
B11 protoporphyrinogen IX oxidase inhibitors:
  diphenyl ethers, in particular acifluorfen;
  cyclic imides, in particular carfentrazone-ethyl or cinidon-ethyl, preferably carfentrazone-ethyl;
B12 photosynthesis inhibitors:
  pyridate;
  benzothiadiazinones, in particular bentazone;
  dipyridylenes, in particular paraquat-dichloride;
  ureas, in particular diuron or isobroturon, preferably diuron;
  phenols, in particular bromoxynil;
  chloridazon;
  triazines, in particular atrazine or terbutylazine; or
  triazinones, in particular metribuzin;
B14 growth substances:
  aryloxyalkanoic acids, in particular MCPA;
  benzoic acids, in particular dicamba;
  quinolinecarboxylic acids, in particular quinclorac.

The following embodiments are especially preferred with a view to the synergistic herbicidal action of the mixtures according to the invention:

In a particular embodiment, the synergistic herbicidal mixture according to the invention comprises, as component A), a 3-heterocyclyl-substituted benzoyl derivative of the formula I, where $R^2$ is a heterocyclic radical selected from the group: isoxazol-3-yl, isoxazol-5-yl and 4,5-dihydroisoxazol-3-yl, the three radicals mentioned being unsubstituted or mono- or polysubstituted by halogen, $C_1$–$C_4$-alkyl, $C_1$–$C_4$-alkoxy, $C_1$–$C_4$-haloalkyl, $C_1$–$C_4$-haloalkoxy or $C_1$–$C_4$-alkylthio; in particular isoxazol-5-yl, 3-methyl-isoxazol-5-yl, 4,5-dihydroisoxazol-3-yl, 5-methyl-4,5-dihydroisoxazol-3-yl, 5-ethyl-4,5-dihydroisoxazol-3-yl or 4,5-dimethyl-4,5-dihydroisoxazol-3-yl;

and, as component B), at least one herbicidal compound from amongst the groups B1, B2, B4 to B12 and B14; in particular clodinafop (and, if appropriate, cloquintocet), diflufenzopyr, imazethapyr, flumetsulam, pyrithiobac-sodium, nicosulfuron, N-[[[4-methoxy-6-(trifluoromethyl)-1,3,5-triazin-2-yl]amino]-carbonyl]-2-(trifluoromethyl)benzene-sulfonamide, clopyralid, 2,4-D, isoxaflutole, glyphosate, glufosinate-ammonium, dimethenamide, S-dimethenamide, acetochlor, metolachlor, S-metolachlor, pendimethalin, carfentrazone-ethyl, pyridate, bentazone, diuron, bromoxynil, atrazine, terbutylazine, metribuzine or dicamba.

Very particularly preferred are mixtures which comprise, as component A), 4-[2-chloro-3-(4,5-dihydroisoxazol-3-yl)-4-methylsulfonylbenzoyl]-1-methyl-5-hydroxy-1H-pyrazole.

Very particularly preferred are also mixtures which comprise, as component A), 4-[2-methyl-3-(4,5-dihydroisoxazol-3-yl)-4-methylsulfonylbenzoyl]-1-methyl-5-hydroxy-1H-pyrazole.

Very particularly preferred are also mixtures which comprise, as component A), 4-[2-chloro-3-(3-methyl-isoxazol-5-yl)-4-methylsulfonylbenzoyl]-1-methyl-5-hydroxy-1H-pyrazole.

In another particular embodiment, the synergistic herbicidal mixture according to the invention comprises, as component A), a 3-heterocyclyl-substituted benzoyl derivative of the formula I where $R^2$ is a heterocyclic radical selected from the group: thiazol-2-yl, thiazol-4-yl, thiazol-5-yl, isoxazol-4-yl, 4,5-dihydroisoxazol-4-yl and 4,5-dihydroisoxazol-5-yl, it being possible for the six radicals mentioned to be unsubstituted or mono- or polysubstituted by halogen, $C_1$–$C_4$-alkyl, $C_1$–$C_4$-alkoxy, $C_1$–$C_4$-haloalkyl, $C_1$–$C_4$-haloalkoxy or $C_1$–$C_4$-alkylthio;

and, as component B), at least one herbicidal compound from amongst the groups B1, B2, B4 to B12 and B14; in particular clodinafop (and, if appropriate, cloquintocet), diflufenzopyr, imazethapyr, flumetsulam, pyrithiobac-sodium, nicosulfuron, N-[[[4-methoxy-6-(trifluoromethyl)-1,3,5-triazin-2-yl]amino]-carbonyl]-2-(trifluoromethyl)benzene-sulfonamide, clopyralid, 2,4-D, isoxaflutole, glyphosate, glufosinate-ammonium, dimethenamide, S-dimethenamide, acetochlor, metolachlor, S-metolachlor, pendimethalin, carfentrazone-ethyl, pyridate, bentazone, diuron, bromoxynil, atrazine, terbutylazine, metribuzine or dicamba.

In a further particular embodiment, the synergistic herbicidal mixture according to the invention comprises, as component A), a 3-heterocyclyl-substituted benzoyl derivative of the formula I where $R^2$ is a heterocyclic radical selected from the group consisting of 4,5-dihydroisoxazol-3-yl, 4,5-dihydroisoxazol-4-yl and 4,5-dihydroisoxazol-5-yl, where the three abovementioned radicals may be unsubstituted or mono- or polysubstituted by halogen, $C_1$–$C_4$-alkyl, $C_1$–$C_4$-alkoxy, $C_1$–$C_4$-haloalkyl, $C_1$–$C_4$-haloalkoxy or $C_1$–$C_4$-alkylthio;

and as component B) at least one herbicidal compound from amongst the groups B1, B2, B4 to B12 and B14;

The synergistic herbicidal mixture according to the invention preferably comprises, as component B), at least one herbicidal compound from the following groups:

B1 acetyl-CoA carboxylase inhibitors (ACC): cyclohexenone oxime ethers or phenoxypropionic esters;
B2 acetolactate synthase inhibitors (ALS): imidazolinones, pyrimidyl ethers, sulfonamides or sulfonylureas;
B4 auxin herbicides: pyridinecarboxylic acids or 2,4-D;
B5 auxin transport inhibitors;
B6 carotenoid biosynthesis inhibitors;
B7 enolpyruvylshikimate 3-phosphate synthase inhibitors;
B8 glutamine synthetase inhibitors;
B9 lipid biosynthesis inhibitors: chloroacetanilides or thioureas,
B10 mitosis inhibitors: dinitroanilines;
B11 protoporphyrinogen IX oxidase inhibitors: diphenyl ethers, oxadiazoles, cyclic imides or pyrazoles;
B12 photosynthesis inhibitors: pyridate, pyridafol, benzothiadiazinone, dipyridylene, ureas, phenols, chloridazon, triazines or triazinones, in particular pyridate, benzothinediazinone, dipyridylenes, ureas, phenols, chloridazon, triazines or triazinones;
B14 growth substances: aryloxyalkanoic acids, benzoic acids or quinolinecarboxylic acids.

In particular, the synergistic herbicidal mixture according to the invention comprises, as component B), at least one herbicidal compound from the group: cycloxydim, sethoxydim, clodinafop (and, if appropriate, cloquintocet), fenoxaprop-ethyl, fenoxaprop-P-ethyl, imazapyr, imazaquin, imazamethabenz, imazethapyr, pyrithiobac-sodium, metosulam, halosulfuron-methyl, nicosulfuron, N-[[[4-methoxy-6-(trifluoromethyl)-1,3,5-triazin-2-yl]amino]carbonyl]-2-(trifluoromethyl)-benzenesulfonamide, flufenacet, 2,4-D, diflufenzopyr, isoxaflutole, sulcotrione, glyphosate, glufosinate-ammonium, dimethenamid, S-metolachlor, benthiocarb, pendimethalin, acifluorfen, carfentrazone-ethyl, cinidon-ethyl, pyridate, bentazon, paraquat-dichloride, diuron, isoproturon, bromoxynil, chloridazon, atrazine, metribuzin, MCPA, dicamba and quinclorac.

Also preferably, the synergistic herbicidal mixture according to the invention comprises, as component B), at least one herbicidal compound from amongst the groups B1, B2, B4 to B11 and B14;

In particular, the synergistic herbicidal mixture according to the invention comprises at least one herbicidal compound from amongst the following groups:

B1 acetyl-CoA carboxylase inhibitors (ACC): cyclohexenone oxime ethers or phenoxypropionic esters;

B2 acetolactate synthase inhibitors (ALS): imidazolinones, pyrimidyl ethers, sulfonamides or sulfonylureas;

B4 auxin herbicides: 2,4-D;

B5 auxin transport inhibitors;

B6 carotenoid biosynthesis inhibitors;

B7 enolpyruvylshikimate 3-phosphate synthase inhibitors;

B8 glutamine synthetase inhibitors;

B9 lipid biosynthesis inhibitors: chloroacetanilides or thioureas,

B10 mitosis inhibitors: dinitroanilines;

B11 protoporphyrinogen IX oxidase inhibitors: diphenyl ethers, oxadiazoles, cyclic imides or pyrazoles;

B14 growth substances: aryloxyalkanoic acid, benzoic acids or quinolinecarboxylic acids.

The synergistic herbicidal mixture particularly preferably comprises at least one herbicidal compound from amongst the group:

cycloxydim, sethoxydim, clodinafop (and, if appropriate, cloquintocet), fenoxaprop-ethyl, fenoxaprop-P-ethyl, imazapyr, imazaquin, imazamethabenz, imazethapyr, pyrithiobac-sodium, metosulam, halosulfuron-methyl, nicosulfuron, N-[[[4-methoxy-6-(trifluoromethyl)-1,3,5-triazin-2-yl]amino]carbonyl]-2-(trifluoromethyl)-benzenesulfonamide, flufenacet, 2,4-D, diflufenzopyr, isoxaflutole, sulcotrione, glyphosate, glufosinate-ammonium, dimethenamid, S-metolachlor, benthiocarb, pendimethalin, acifluorfen, carfentrazone-ethyl, cinidon-ethyl, MCPA, dicamba and quinclorac.

Also preferably, the synergistic herbicidal mixture according to the invention comprises, as component B), at least one herbicidal compound from amongst the group B12.

The synergistic herbicidal mixture according to the invention comprises in particular at least one herbicidal compound from amongst the group: propanil, pyridate, benzothiadiazinones, dinitrophenols, dipyridylenes, ureas, phenols, chloridazon, triazines, triazinones, uracils and biscarbamates.

Particularly preferably, the synergistic herbicidal mixture according to the invention comprises at least one herbicidal compound from amongst the group: pyridate, bentazone, paraquat-dichloride, diuron, isoproturon, bromoxynil, chloridazon, atrazine or metribuzin.

Also particularly preferably, the herbicidal mixture according to the invention comprises at least one herbicidal compound from amongst the group: propanil, pyridate, dinitrophenols, dipyridylenes, chloridazon, triazinones, uracils and biscarbamates.

Particularly preferably, the synergistic herbicidal mixture according to the invention comprises at least one compound from amongst the group: pyridate, paraquat-dichloride, chloridazon or metribuzin.

In a further particular embodiment, the synergistic herbicidal mixture according to the invention comprises, as component A), a 3-heterocyclyl-substituted benzoyl derivative of the formula I where $R^2$ is a heterocyclic radical selected from the group consisting of thiazol-2-yl, thiazol-4-yl and thiazol-5-yl, where the three abovementioned radicals may be unsubstituted or mono- or polysubstituted by halogen, $C_1$–$C_4$-alkyl, $C_1$–$C_4$-alkoxy, $C_1$–$C_4$-haloalkyl, $C_1$–$C_4$-haloalkoxy or $C_1$–$C_4$-alkylthio;

and, as component B), at least one herbicidal compound from amongst the groups B1, B2, B4 to B12 or B14;

The synergistic herbicidal mixture according to the invention preferably comprises, as component B), at least one herbicidal compound from the following groups:

B1 acetyl-CoA carboxylase inhibitors (ACC): cyclohexenone oxime ethers or phenoxypropionic esters;

B2 acetolactate synthase inhibitors (ALS): imidazolinones, pyrimidyl ethers, sulfonamides or sulfonylureas;

B4 auxin herbicides: pyridinecarboxylic acids or 2,4-D;

B5 auxin transport inhibitors;

B6 carotenoid biosynthesis inhibitors;

B7 enolpyruvylshikimate 3-phosphate synthase inhibitors;

B8 glutamine synthetase inhibitors;

B9 lipid biosynthesis inhibitors: chloroacetanilides or thioureas,

B10 mitosis inhibitors: dinitroanilines;

B11 protoporphyrinogen IX oxidase inhibitors: diphenyl ethers, oxadiazoles, cyclic imides or pyrazoles;

B12 photosynthesis inhibitors: pyridate, pyridafol, benzothiadiazinones, dipyridylenes, ureas, phenols, chloridazon, triazines or triazinones, in particular pyridate, benzothiadiazinones, dipyridylenes, ureas, phenols, chloridazon, triazines or triazinones;

B14 growth substances: aryloxyalkanoic acids, benzoic acids or quinolinecarboxylic acids.

In particular, the synergistic herbicidal mixture according to the invention comprises, as component B), at least one herbicidal compound from the group:

cycloxydim, sethoxydim, clodinafop (and, if appropriate, cloquintocet), fenoxaprop-ethyl, fenoxaprop-P-ethyl, imazapyr, imazaquin, imazamethabenz, imazethapyr, pyrithiobac-sodium, metosulam, halosulfuron-methyl, nicosulfuron, N-[[[4-methoxy-6-(trifluoromethyl)-1,3,5-triazin-2-yl]amino]carbonyl]-2-(trifluoromethyl)-benzenesulfonamide, flufenacet, 2,4-D, diflufenzopyr, isoxaflutole, sulcotrione, glyphosate, glufosinate-ammonium, dimethenamid, S-metolachlor, benthiocarb, pendimethalin, acifluorfen, carfentrazone-ethyl, cinidon-ethyl, pyridate, bentazon, paraquat-dichloride, diuron, isoproturon, bromoxynil, chloridazon, atrazine, metribuzin, MCPA, dicamba and quinclorac.

Also preferably, the synergistic herbicidal mixture according to the invention comprises, as component B), at least one herbicidal compound from amongst the groups B1, B2, B4 to B11 and B14;

In particular, the synergistic herbicidal mixture according to the invention comprises at least one herbicidal compound from amongst the following groups:

B1 acetyl-CoA carboxylase inhibitors (ACC): cyclohexenone oxime ethers or phenoxypropionic esters;

B2 acetolactate synthase inhibitors (ALS): imidazolinones, pyrimidyl ethers, sulfonamides or sulfonylureas;

B4 auxin herbicides: 2,4-D;

B5 auxin transport inhibitors;

B6 carotenoid biosynthesis inhibitors;

B7 enolpyruvylshikimate 3-phosphate synthase inhibitors;

B8 glutamine synthetase inhibitors;

B9 lipid biosynthesis inhibitors: chloroacetanilides or thioureas,

B10 mitosis inhibitors: dinitroanilines;

B11 protoporphyrinogen IX oxidase inhibitors: diphenyl ethers, oxadiazoles, cyclic imides or pyrazoles;

B14 growth substances: aryloxyalkanoic acid, benzoic acids or quinolinecarboxylic acids.

The synergistic herbicidal mixture particularly preferably comprises at least one herbicidal compound from amongst the group:

cycloxydim, sethoxydim, clodinafop (and, if appropriate, cloquintocet), fenoxaprop-ethyl, fenoxaprop-P-ethyl, imazapyr, imazaquin, imazamethabenz, imazethapyr, pyrithiobac-sodium, metosulam, halosulfuron-methyl, nicosulfuron, N-[[[4-methoxy-6-(trifluoromethyl)-1,3,5-triazin-2-yl]amino]carbonyl]-2-(trifluoromethyl)-benzenesulfonamide, flufenacet, 2,4-D, diflufenzopyr, isoxaflutole, sulcotrione, glyphosate, glufosinate-ammonium, dimethenamid, S-metolachlor, benthiocarb, pendimethalin, acifluorfen, carfentrazone-ethyl, cinidon-ethyl, MCPA, dicamba and quinclorac.

Also preferably, the synergistic herbicidal mixture according to the invention comprises, as component B), at least one herbicidal compound from amongst the group B12.

The synergistic herbicidal mixture according to the invention comprises in particular at least one herbicidal compound from amongst the group: propanil, pyridate, benzothiadiazinone, dinitrophenols, dipyridylenes, ureas, phenols, chloridazone, triazines, triazinones, uracils and biscarbamates.

Particularly preferably, the synergistic herbicidal mixture according to the invention comprises at least one herbicidal compound from amongst the group: pyridate, bentazone, paraquat-dichloride, diuron, isoproturon, bromoxynil, chloridazon, atrazine or metribuzin.

Also particularly preferably, the herbicidal mixture according to the invention comprises at least one herbicidal compound from amongst the group: propanil, pyridate, dinitrophenols, dipyridylenes, chloridazon, triazinones, uracils and biscarbamates.

Particularly preferably, the synergistic herbicidal mixture according to the invention comprises at least one compound from amongst the group: pyridate, paraquat-dichloride, chloridazon or metribuzin.

In a further particular embodiment, the synergistic herbicidal mixture according to the invention comprises, as component A), a 3-heterocyclyl-substituted benzoyl derivative of the formula I where $R^2$ is a heterocyclic radical selected from the group consisting of isoxazol-3-yl, isoxazol-4-yl and isoxazol-5-yl, where the three abovementioned radicals may be unsubstituted or mono- or polysubstituted by halogen, $C_1$–$C_4$-alkyl, $C_1$–$C_4$-alkoxy, $C_1$–$C_4$-haloalkyl, $C_1$–$C_4$-haloalkoxy or $C_1$–$C_4$-alkylthio;

and, as component B), at least one herbicidal compound from amongst the groups B1, B2, B4 to B12 or B14;

The synergistic herbicidal mixture according to the invention preferably comprises, as component B), at least one herbicidal compound from the groups B1, B2, B4 to B11 and B14;

In particular, the synergistic herbicidal mixture according to the invention comprises at least one herbicidal compound from the following groups:

B1 acetyl-CoA carboxylase inhibitors (ACC): cyclohexenone oxime ethers or phenoxypropionic esters;

B2 acetolactate synthase inhibitors (ALS): imidazolinones, pyrimidyl ethers, sulfonamides or sulfonylureas;

B4 auxin herbicides: pyridinecarboxylic acids or 2,4-D;

B5 auxin transport inhibitors;

B6 carotenoid biosynthesis inhibitors;

B7 enolpyruvylshikimate 3-phosphate synthase inhibitors;

B8 glutamine synthetase inhibitors;
B9 lipid biosynthesis inhibitors: chloroacetanilides or thioureas,
B10 mitosis inhibitors: dinitroanilines;
B11 protoporphyrinogen IX oxidase inhibitors: diphenyl ethers, oxadiazoles, cyclic imides or pyrazoles;
B14 growth substances: aryloxyalkanoic acid, benzoic acids or quinolinecarboxylic acids.

Particularly preferably, the synergistic herbicidal mixture comprises at least one herbicidal compound from amongst the group:

cycloxydim, sethoxydim, clodinafop (and, if appropriate, cloquintocet), fenoxaprop-ethyl, fenoxaprop-P-ethyl, imazapyr, imazaquin, imazamethabenz, imazethapyr, pyrithiobac-sodium, metosulam, halosulfuron-methyl, nicosulfuron, N-[[[4-methoxy-6-(trifluoromethyl)-1,3,5-triazin-2-yl]amino]carbonyl]-2-(trifluoromethyl)-benzenesulfonamide, flufenacet, 2,4-D, diflufenzopyr, isoxaflutole, sulcotrione, glyphosate, glufosinate-ammonium, dimethenamid, S-metolachlor, benthiocarb, pendimethalin, acifluorfen, carfentrazone-ethyl, cinidon-ethyl, MCPA, dicamba and quinclorac.

Also preferably, the herbicidal mixture according to the invention comprises at least one herbicidal compound from amongst the group: propanil, pyridate, dinitrophenols, dipyridylenes, chloridazon, triazinones, uracils and biscarbamates.

In particular, the synergistic herbicidal mixture according to the invention comprises at least one compound from amongst the group: pyridate, paraquat-dichloride, chloridazon or metribuzin.

In a further particular embodiment, the synergistic herbicidal mixture comprises, as component A, a 3-heterocyclyl-substituted benzoyl derivative of the formula I and, as component B, a herbicidal compound. For particularly preferred embodiments, the preferences described above apply analogously.

In a further particular embodiment, the synergistic herbicidal mixture comprises, as component A, a 3-heterocyclyl-substituted benzoyl derivative of the formula I and, as component B, two herbicidal compounds. For particularly preferred embodiments, the preferences described above apply analogously.

In a further particularly preferred embodiment, the synergistic herbicidal mixture comprises, as component B, a herbicidal compound, where with respect to the preferred embodiments the above preferences apply, and a herbicidal compound from amongst the groups B12 and B14.

The present invention also extends to herbicidal compositions which comprise a herbicidally active amount of a synergistic herbicidal mixture (comprising components A) and B) as described above), at least one liquid and/or solid carrier and, if desired, at least one surfactant.

The herbicidal compositions and synergistic herbicidal mixtures according to the invention can effect very good control of broad-leaved weeds and grass weeds in crops such as maize, cereals, rice and soya without damaging the crop plants, an effect observed especially even at low rates of application.

Taking into consideration the variety of application methods in question, the herbicidal compositions and synergistic herbicidal mixtures according to the invention can additionally be employed in a further number of crop plants for eliminating undesirable plants. Examples of suitable crops are the following: Allium cepa, Ananas comosus, Arachis hypogaea, Asparagus officinalis, Beta vulgaris spp. [sic] altissima, Beta vulgaris spp. [sic] rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicago sativa, Musa spp., Nicotiana tabacum (N.rustica), Olea europaea, Oryza sativa, Phaseolus lunatus, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera und Zea mays.

Moreover, the herbicidal compositions and synergistic herbicidal mixtures according to the invention can also be used in crops which tolerate the action of herbicides due to breeding, including genetic engineering methods.

The mixtures according to the invention, or the herbicidal compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring.

The use forms depend on the intended purposes; in any case, they should guarantee the finest possible distribution of the active ingredients according to the invention.

Suitable inert auxiliaries are mineral oil fractions of medium to high boiling point such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, such as N-methylpyrrolidone and water.

Aqueous use forms can be prepared from emulsion concentrates, suspensions, pastes, wettable powders or water-dispersible granules by adding water. To prepare emulsions, pastes or oil dispersions, the substrates [sic], as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Suitable surfactants are the alkali metal, alkaline earth metal and ammonium salts of aromatic sulfonic acids, e.g. ligno-, phenol-, naphthalene- and dibutylnaphthalenesulfonic acid, and of fatty acids, of alkyl- and alkylaryl sulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl and tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the synergistic herbicidal mixture or the individual active ingredients with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the mixtures according to the invention in the ready-to-use products can be varied within wide ranges. In general, the formulations comprise from 0.01 to 95% by weight, preferably 0.5 to 90% by weight, of the mixture according to the invention.

The active ingredients of components A) and B) can be formulated jointly, but also separately, and/or applied to the plants, their environment and/or seeds jointly or separately. It is preferable to apply the active ingredients simultaneously. However, it is also possible to apply them separately.

Moreover, it may be advantageous to apply the herbicidal compositions and synergistic herbicidal mixtures according to the invention, jointly or separately, with additional other crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates can also be added.

The mixtures according to the invention and the herbicidal compositions can be applied pre- or post-emergence. If the active ingredients are less well tolerated by certain crop plants, application techniques may be used in which the herbicidal compositions are sprayed, with the aid of the spray apparatus, in such a way that they come into as little contact, if any, with the leaves of the sensitive crop plants while reaching the leaves of undesirable plants which grow underneath, or the bare soil (post-directed, lay-by).

In the case of a post-emergence treatment of the plants, the herbicidal compositions according to the invention are preferably applied by foliar application. Application may be effected, for example, by usual spraying techniques with water as the carrier, using amounts of spray mixture of approx. 100 to 1000 l/ha. The compositions may also be applied by the so-called "low-volume" and "ultra-low-volume" methods, or in the form of so-called granules.

As a rule, the synergistic herbicidal mixtures comprise components A) and B) in such weight ratios that the synergistic effect takes place. The ratios of component A) and B) in the mixture preferably range from 1:0.002 to 1:800, preferably from 1:0.003 to 1:160, particularly preferably from 1:0.02 to 1:160.

In particular, the mixtures according to the invention comprise a 3-heterocyclyl-substituted benzoyl derivative of the formula I and a herbicidal compound from the Group B1 (acetyl-CoA carboxylase inhibitors (ACC)) in a weight ratio of 1:0.1 to 1:80, preferably of 1:0.17 to 1:16.

The mixtures according to the invention especially preferably comprise a 3-heterocyclyl-substituted benzoyl derivative of the formula I and a herbicidal compound from the group of the cyclohexenone oxime ethers, preferably cycloxydim, sethoxydim or tralkoxydim, in particular sethoxydim or tralkoxydim, in a weight ratio of 1:0.4 to 1:80, preferably 1:0.67 to 1:16.

Also, the mixtures according to the invention especially preferably comprise a 3-heterocyclyl-substituted benzoyl derivative of the formula I and a herbicidal compound from the group of the phenoxyphenoxypropionic esters in a weight ratio of 1:0.1 to 1:60, preferably from 1:0.17 to 1:12.

Very particularly preferably, they comprise, as component B), clodinafop-propargyl in a weight ratio of 1:0.1 to 1:20, preferably 1:0.17 to 1:4.

Also very particularly preferably, they comprise, as component B), fenoxaprop-ethyl in a weight ratio of 1:0.2 to 1:60, preferably 1:0.34 to 1:12.

Also very particularly preferably, they comprise, as component B), fenoxaprop-P-ethyl in a weight ratio of 1:0.1 to 1:30, preferably 1:0.16 to 1:6.

Also in particular, the mixtures according to the invention comprise a 3-heterocyclyl-substituted benzoyl derivative of the formula I and a herbicidal compound from the Group B2 (acetolactate synthase inhibitors) in a weight ratio of 1:0.004 to 1:160, preferably 1:0.006 to 1:32.

Especially preferably, the mixtures according to the invention comprise 3-heterocyclyl-substituted benzoyl derivative of the formula I and a herbicidal compound from the group of the imidazolinones in a weight ratio of 1:0.08 to 1:160, preferably 1:0.13 to 1:32.

Very particularly preferably, they comprise, as component B), imazapyr in a weight ratio of 1:0.12 to 1:80, preferably 1:0.2 to 1:16.

Also very particularly preferably, they comprise, as component B), imazaquin in a weight ratio of 1:0.2 to 1:60, preferably 1:0.33 to 1:12.

Also very particularly preferably, they comprise, as component B), imazamethabenz in a weight ratio of 1:0.4 to 1:160, preferably 1:0.66 to 1:32.

Also very particularly preferably, they comprise, as component B), imazethapyr in a weight ratio of 1:0.12 to 1:30, preferably 1:0.2 to 1:6.

Also especially preferably, the mixtures according to the invention comprise a 3-heterocyclyl-substituted benzoyl derivative of the formula I and a herbicidal compound from the group of the pyrimidyl ethers, in particular pyrithiobac-sodium, in a weight ratio of 1:0.008 to 1:24, preferably 1:0.013 to 1:4.8.

Also-especially preferably, the mixtures according to the invention comprise a 3-heterocyclyl-substituted benzoyl derivative of the formula I and a herbicidal compound from amongst the group of the sulfonamides in a weight ratio of 1:0.004 to 1:45, preferably 1:0.006 to 1:9.

Very particularly preferably, they comprise, as component B), flumetsulam in a weight ratio of 1:0.1 to 1:45, preferably 1:0.17 to 1:9.

Also very particularly preferably, they comprise, as component B), metosulam in a weight ratio of 1:0.004 to 1:12, preferably 1:0.006 to 1:2.4.

Also especially preferably, the mixtures according to the invention comprise a 3-heterocyclyl-substituted benzoyl derivative of the formula I and a herbicidal compound from the group of the sulfonylureas in a weight ratio of 1:0.004 to 1:24, preferably 1:0.006 to 1:4.8.

Very particularly preferably, they comprise, as component B), halosulfuron-methyl, rimsulfuron or N-[[[4-methoxy-6-(trifluoromethyl)-1,3,5-triazin-2-yl]amino]carbonyl]-2-(trifluoromethyl) benzenesulfonamide in a weight ratio of 1:0.02 to 1:24, preferably 1:0.03 to 1:4.8.

Also very particularly preferably, they comprise, as component B), nicosulfuron in a weight ratio of 1:0.02 to 1:24, preferably 1:0.03 to 1:4.8.

Also very particularly preferably, they comprise, as component B), primisulfuron-methyl or prosulfuron in a weight ratio of 1:0.04 to 1:24, preferably 1:0.06 to 1:4.8.

Also very particularly preferably, they comprise, as component B), thifensulfuron-methyl, tribenuron-methyl or sulfosulfuron in a weight ratio of 1:0.04 to 1:12, preferably 1:0.06 to 1:2.4.

Also in particular, the mixtures according to the invention comprise a 3-heterocyclyl-substituted benzoyl derivative of the formula I and a herbicidal compound from the Group B3 (amides), in particular fluthiamide, in a weight ratio of 1:1 to 1:400, preferably 1:0.6 to 1:80.

Also in particular, the mixtures according to the invention comprise a 3-heterocyclyl-substituted benzoyl derivative of the formula I and a herbicidal compound from the Group B4 (auxin-herbicides) in a weight ratio of 1:0.1 to 1:150, preferably 1:0.67 to 1:30.

Especially preferably, the mixtures according to the invention comprise a 3-heterocyclyl-substituted benzoyl derivative of the formula I and a herbicidal compound from amongst the group of the pyridinecarboxylic acids, in particular clopyralid, in a weight ratio of 1:0.1 to 1:150, preferably 1:0.67 to 1:30.

Also especially preferably, the mixtures according to the invention comprise a 3-heterocyclyl-substituted benzoyl derivative of the formula 1 and 2,4-D in a weight ratio of 1:0.2 to 1:150, preferably 1:0.33 to 1:30.

Also in particular, the mixtures according to the invention comprise a 3-heterocyclyl-substituted benzoyl derivative of the formula I and a herbicidal compound from the Group B5 (auxin transport inhibitors), preferably diflufenzopyr, in a weight ratio of 1:0.06 to 1:20, preferably 1:0.1 to 1:4.

Also in particular, the mixtures according to the invention comprise a 3-heterocyclyl-substituted benzoyl derivative of the formula I and a herbicidal compound from the Group B6 (carotenoid biosynthesis inhibitors) in a weight ratio of 1:0.1 to 1:120, preferably 1:0.17 to 1:24.

Especially preferably, the mixtures according to the invention comprise a 3-heterocyclyl-substituted benzoyl derivative of the formula I and isoxaflutole or isoxachlortole in a weight ratio of 1:0.1 to 1:40, preferably 1:0.17 to 1:8.

Also especially preferred, the mixtures according to the invention comprise a 3-heterocyclyl-substituted benzoyl derivative of the formula I and mesotrione or ketospiradox in a weight ratio of 1:0.1 to 1:60, preferably 1:0.16 to 1:12.

Also especially preferred, the mixtures according to the invention comprise a 3-heterocyclyl-substituted benzoyl derivative of the formula I and sulcotrione in a weight ratio of 1:0.4 to 1:120, preferably 1:0.66 to 1:24.

Also in particular, the mixtures according to the invention comprise a 3-heterocyclyl-substituted benzoyl derivative of the formula I and a herbicidal compound from the Group B7 (enolpyruvylshikimate-3-phosphate synthase inhibitors (ESPS)), preferably glyphosate or sulfosate, in a weight ratio of 1:1.4 to 1:216, preferably 1:2.4 to 1:43.2.

Also in particular, the mixtures according to the invention comprise a 3-heterocyclyl-substituted benzoyl derivative of the formula I and a herbicidal compound from the group B8 (glutamine synthetase inhibitors), preferably glufosinate-ammonium, in a weight ratio of 1:0.04 to 1:120, preferably 1:0.06 to 1:24.

Also in particular, the mixtures according to the invention comprise a 3-heterocyclyl-substituted benzoyl derivative of the formula I and a herbicidal compound from the group B9 (lipid biosynthesis inhibitors) in a weight ratio of 1:0.24 to 1:800, preferably 1:0.40 to 1:160.

Especially preferably, the mixtures according to the invention comprise a 3-heterocyclyl-substituted benzoyl derivative of the formula I and a herbicidal compound from the group of the chloroacetanilides in a weight ratio of 1:0.24 to 1:800, preferably 1:0.4 to 1:160.

Very particularly preferably, the mixtures according to the invention comprise a 3-heterocyclyl-substituted benzoyl derivative of the formula I and dimethenamid or S-dimethenamid in a weight ratio of 1:0.24 to 1:400, preferably 1:0,4 to 1:80.

Also very particularly preferably, the mixtures according to the invention comprise a 3-heterocyclyl-substituted benzoyl derivative of the formula I and acetochlor in a weight ratio of 1:1 to 1:800, preferably 1:1.67 to 1:160.

Also very particularly preferably, the mixtures according to the invention comprise a 3-heterocyclyl-substituted benzoyl derivative of the formula I and metolachlor or S-metolachlor in a weight ratio of 1:0.24 to 1:800, preferably 1:0.40 to 1:160.

Especially preferably, the mixtures according to the invention comprise a 3-heterocyclyl-substituted benzoyl derivative of the formula I and a herbicidal compound from the group of the thioureas in a weight ratio of 1:0.4 to 1:800, preferably 1:0.66 to 1:160.

Very particularly preferably, the mixtures according to the invention comprise a 3-heterocyclyl-substituted benzoyl derivative of the formula I and benthiocarb in a weight ratio of 1:4 to 1:800, preferably 1:6.6 to 1:160.

Also in particular, the mixtures according to the invention comprise a 3-heterocyclyl-substituted benzoyl derivative of the formula I and a herbicidal compound from the group B10 (mitosis inhibitors), preferably a dinitroaniline, in particular pendimethalin, in a weight ratio of 1:1,5 to 1:600, preferably 1:2,5 to 1:120.

Also in particular, the mixtures according to the invention comprise a 3-heterocyclyl-substituted benzoyl derivative of the formula I and a herbicidal compound from the group B11 (protoporphyrinogen IX oxidase inhibitors) in a weight ratio of 1:0.002 to 1:120, preferably 1:0.003 to 1:24.

Especially preferably, the mixtures according to the invention comprise 3-heterocyclyl-substituted benzoyl derivative of the formula I and a herbicidal compound from the group of the diphenylethers, in particular acifluorfen or acifluorfen-sodium, in a weight ratio of 1:0.2 to 1:60, preferably 1:0.33 to 1:12.

Also especially preferably, the mixtures according to the invention comprise a 3-heterocyclyl-substituted benzoyl derivative of the formula I and a herbicidal compound from the group of the oxadiazoles, in particular oxadiargyl, in a weight ratio of 1:0.2 to 1:120, preferably 1:0.33 to 1:24.

Also especially preferably, the mixtures according to the invention comprise a 3-heterocyclyl-substituted benzoyl derivative of the formula I and a herbicidal compound from the group of the cyclic imides in a weight ratio of 1:0.002 to 1:60, preferably 1:0.003 to 1:12.

Very particularly preferably, the mixtures according to the invention comprise a 3-heterocyclyl-substituted benzoyl derivative of the formula I and carfentrazone-ethyl in a weight ratio of 1:0.002 to 1:7, preferably 1:0.003 to 1:1.4.

Also very particularly preferably, the mixtures according to the invention comprise a 3-heterocyclyl-substituted benzoyl derivative of the formula I cinidon-ethyl or flumiclorac-pentyl, in a weight ratio of 1:0.012 to 1:7, preferably 1:0.02 to 1:1.4.

Also very particularly preferably, the mixtures according to the invention comprise a 3-heterocyclyl-substituted benzoyl derivative of the formula I and butafenacil in a weight ratio of 1:0.02 to 1:60, preferably 1:0.03 to 1:12.

Also very particularly preferably, the mixtures according to the invention comprise a 3-heterocyclyl-substituted benzoyl derivative of the formula I and JV 485 in a weight ratio of 1:0.2 to 1:60, preferably 1:0.3 to 1:12.

In particular, the mixtures according to the invention comprise a 3-heterocyclyl-substituted benzoyl derivative of the formula I and a herbicidal compound from group B12 (photosynthesis inhibitors) in a weight ratio of 1:0.12 to 1:800, preferably 1:0.2 to 1:160.

Especially preferably, the mixtures according to the invention comprise a 3-heterocyclyl-substituted benzoyl derivative of the formula I and pyridate or pyridafol in a weight ratio of 1:1 to 1:300, preferably 1:1.67 to 1:60.

Also especially preferably, the mixtures according to the invention comprise a 3-heterocyclyl-substituted benzoyl derivative of the formula I and a herbicidal compound from the group of the benzothiadiazinones, in particular bentazone, in a weight ratio of 1:1.92 to 1:288, preferably 1:3.2 to 1:57.6.

Also especially preferably, the mixtures according to the invention comprise a 3-heterocyclyl-substituted benzoyl derivative of the formula I and a herbicidal compound from the group of the dipyridylenes, in particular paraquat-dichloride, in a weight ratio of 1:0.4 to 1:160, preferably 1:0.66 to 1:32.

Also especially preferably, the mixtures according to the invention comprise a 3-heterocyclyl-substituted benzoyl derivative of the formula I and a herbicidal compound from the group of the ureas, in particular diuron or isoproturon, in a weight ratio of 1:1 to 1:320, preferably 1:1.67 to 1:64.

Also especially preferably, the mixtures according to the invention comprise a 3-heterocyclyl-substituted benzoyl derivative of the formula I and a herbicidal compound from the group of the phenols, in particular bromoxynil, in a weight ratio of 1:0.4 to 1:140, preferably 1:0.67 to 1:28.

Also especially preferably, the mixtures according to the invention comprise a 3-heterocyclyl-substituted benzoyl derivative of the formula I and chloridazon in a weight ratio of 1:2 to 1:800, preferably 1:3.3 to 1:160.

Also especially preferably, the mixtures according to the invention comprise a 3-heterocyclyl-substituted benzoyl derivative of the formula I and a herbicidal compound from the group of the triazines, in particular atrazine or terbutylazine, in a weight ratio of 1:1 to 1:800, preferably 1:1.67 to 1:160.

Also especially preferably, the mixtures according to the invention comprise a 3-heterocyclyl-substituted benzoyl derivative of the formula I and a herbicidal-compound from the group of the triazinones, in particular metribuzin, in a weight ratio of 1:0.12 to 1:60, preferably 1:0.2 to 1:12.

Also in particular, the mixtures according to the invention comprise a 3-heterocyclyl-substituted benzoyl derivative of the formula I and a herbicidal compound from the group B13 (synergists), preferably an oxirane, in particular tridiphane, in a weight ratio of 1:2 to 1:300, preferably 1:3.33 to 1:60.

Also in particular, the mixtures according to the invention comprise a 3-heterocyclyl-substituted benzoyl derivative of the formula I and a herbicidal compound from the group B14 (growth substances) in a weight ratio of 1:0.1 to 1:240, preferably 1:0.167 to 1:48.

Especially preferably, the mixtures according to the invention comprise a 3-heterocyclyl-substituted benzoyl derivative of the formula I and a herbicidal compound from the group of the aryloxyalkanoic acids in a weight ratio of 1:0.2 to 1:240, preferably 1:0,33 to 1:48.

Very particularly preferably, they comprise, as component B) fluoroxypyr in a weight ratio of 1:0.2 to 1:80, preferably 1:0.33 to 1:16.

Also very particularly preferably, they comprise, as component B), MCPA or mecoprop-P in a weight ratio of 1:1.6 to 1:240, preferably 1:2.67 to 1:48.

Also especially preferably, the mixtures according to the invention comprise a 3-heterocyclyl-substituted benzoyl derivative of the formula I and a herbicidal compound from the group of the benzoic acids, in particular dicamba, in a weight ratio of 1:0.3 to 1:160, preferably 1:0.5 to 1:32.

Also especially preferably, the mixtures according to the invention comprise a 3-heterocyclyl-substituted benzoyl derivative of the formula I and a herbicidal compound from the group of the quinolinecarboxylic acids, in particular quinclorac, in a weight ratio of 1:0,1 to 1:120, preferably 1:0.16 to 1:24.

Also in particular, the mixtures according to the invention comprise a 3-heterocyclyl-substituted benzoyl derivative of the formula I and a herbicidal compound from the group B16 (various other herbicides), in particular triaziflam, in a weight ratio of 1:0.2 to 1:150, preferably 1:0.3 to 1:30.

Also in particular, the mixtures according to the invention comprise a 3-heterocyclyl-substituted benzoyl derivative of the formula I and two herbicidal compounds from the groups B1 to B16, where the weight ratio of the 3-heterocyclyl-substituted benzoyl derivative of the formula I to each of the individual herbicidal components of B) is in the ranges described above.

Especially preferably, the mixtures according to the invention comprise a 3-heterocyclyl-substituted benzoyl derivative of the formula I, a herbicidal compound from the group B2 and a herbicidal compound from the group B14 in a weight ratio of 1:0.004:0.1 to 1:160:240, preferably 1:0.006:0.16 to 1:32:48.

Especially preferably, the mixtures according to the invention comprise a 3-heterocyclyl-substituted benzoyl derivative of the formula I, a herbicidal compound from the group B5 and a herbicidal compound from the group B14 in a weight ratio of 1:0.06:0.1 to 1:20:240, preferably 1:0.1:0.16 to 1:4:48.

Also especially preferably, the mixtures according to the invention comprise a 3-heterocyclyl-substituted benzoyl derivative of the formula I, a herbicidal compound from the group B9 and a herbicidal compound from the group B12 in a weight ratio of 1:0.24:0.12 to 1:80:800, preferably 1:0.48:0.2 to 1:16:160.

Also especially preferably, the mixtures according to the invention comprise a 3-heterocyclyl-substituted benzoyl derivative of the formula I, a herbicidal compound from the group B12 and a herbicidal compound likewise from the group B12 in a weight ratio of 1:0.12:0.12 to 1:800:800, preferably 1:0.2:0.2 to 1:160:160.

Also especially preferably, the mixtures according to the invention comprise a 3-heterocyclyl-substituted benzoyl derivative of the formula I, a herbicidal compound from the group B12 and a herbicidal compound from the group B14 in a weight ratio of 1:0.12:0.1 to 1:800:240, preferably 1:0.2:0.16 to 1:160:48.

The rate of application of pure synergistic herbicidal mixture, i.e. without formulation auxiliaries, amounts to 2 to 5000 g/ha, preferably 2 to 4500 g/ha, in particular 8 to 4500 g/ha, of active substance (a.s.), depending on the intended aim, the season, the target plants and growth stage.

The rate of application of 3-heterocyclyl-substituted benzoyl derivative of the formula I is 0.1 to 250 g/ha, as a rule 5 to 250 g/ha, preferably 25 to 150 g/ha, of active substance (a.s.).

The preferred rate of application of the individual classes of active ingredients, or of the active ingredients of component B, are compiled in Table 2.

TABLE 2

| Component B | Class of active ingredient | Active ingredient | Rate of application (g/ha) |
|---|---|---|---|
| B1 Acetyl-CoA carboxylase inhibitors | cyclohexenone oxime ethers | | 25–400 |
| | | | 100–400 |
| | | cycloxydim | 100–400 |
| | | sethoxydim | 100–400 |
| | | tralkoxydim | 100–400 |
| | phenoxyphenoxypropionic esters | | 25–300 |
| | | clodinafpop-P-propargyl[a] | 25–100 |
| | | fenoxaprop-ethyl | 50–300 |
| | | fenoxaprop-P-ethyl | 25–150 |
| B2 Acetolactate synthase inhibitors (ALS) | | | 1–800 |
| | imidazolinones | | 20–800 |
| | | imazapyr | 30–400 |
| | | imazaquin | 50–300 |
| | | imazamethabenz | 100–800 |
| | | imazaethopyr | 30–150 |
| | | imazamox | 20–120 |
| | pyrimidyl ethers | | 2–120 |
| | | pyrithiobac-sodium | 2–120 |
| | sulfonamides | | 1–225 |
| | | florasulam | 1–20 |
| | | flumetsulam | 25–225 |
| | | metosulam | 1–60 |
| | sulfonylureas | | 1–120 |
| | | halosulfuron-methyl | 5–120 |
| | | nicosulfuron | 1–120 |
| | | primisulfuron-methyl | 10–120 |
| | | prosulfuron | 10–120 |
| | | rimsulfuron | 5–120 |
| | | thifensulfuron-methyl | 10–60 |
| | | tribenuron-methyl | 10–60 |

TABLE 2-continued

| Component B | Class of active ingredient | Active ingredient | Rate of application (g/ha) |
|---|---|---|---|
| | | N-[[[4-methoxy-6-(trifluoromethyl)-1,3,5-triazin-2-yl]amino]carbonyl]-2-(trifluoromethyl)benzenesulfonamide | 5–120 |
| | | sulfosulfuron | 10–60 |
| B3 Amides | | | 250–2000 |
| | — | fluthiamide | 250–2000 |
| B4 Auxin herbicides | | | 25–750 |
| | pyridinecarboxylic acids | | 25–750 |
| | | clopyralid | 25–750 |
| | — | 2,4-D | 50–750 |
| B5 Auxin transport inhibitors | | | 15–100 |
| | — | diflufenzopyr | 15–100 |
| B6 Carotenoid biosynthesis inhibitors | | | 25–600 |
| | — | isoxaflutole | 25–200 |
| | — | sulcotrione | 100–600 |
| | — | mesotrione | 25–300 |
| | — | isoxachlortole | 25–200 |
| | — | ketospiradox | 25–300 |
| B7 Enolpyruvylshikimat-3-phosphate synthase inhibitors (ESPS) | | | 360–1080 |
| | — | glyphosate | 360–1080 |
| | — | sulfosate | 360–1080 |
| B8 Glutamine synthetase inhibitors | | | 10–600 |
| | — | glufosinate-ammonium | 10–600 |
| B9 Lipid biosynthesis inhibitors | | | 60–4000 |
| | chloroacetanilides | | 60–4000 |
| | | dimethenamid | 60–4000 |
| | | S-dimethenamid | 60–2000 |
| | | acetochlor | 60–2000 |
| | | metolachlor | 250–4000 |
| | | S-metolachlor | 60–4000 |
| | thioureas | | 60–4000 |
| | | benthiocarb | 100–4000 |
| B10 Mitosis inhibitors | | | 1000–4000 |
| | dinitroanilines | | 375–3000 |
| | | pendimethalin | 375–3000 |
| B11 Protophorphyrinogen [sic] IX oxidase inhibitors | | | 375–3000 |
| | | | 0.5–600 |
| | diphenyl ethers | | 50–300 |
| | | acifluorfen | 50–300 |
| | | acifluorfen-sodium | 50–300 |
| | oxadiazoles | | 50–600 |
| | | oxadiargyl | 50–600 |
| | cyclic imides | | 0.5–300 |
| | | carfentrazone-ethyl | 0.5–35 |
| | | cinidon-ethyl | 3–35 |
| | | flumiclorac-pentyl | 3–35 |
| | | butafenacil | 5–300 |
| | | JV 485 | 50–300 |
| B12 Photosynthesis inhibitors | | | 30–4000 |
| | — | pyridate | 250–1500 |
| | | pyridafol | 250–1000 |
| | benzothiadiazinones | | 480–1440 |
| | | bentazone | 480–1440 |
| | dipyridylenes | | 100–800 |
| | | paraquat-dichloride | 100–800 |
| | ureas | | 250–1600 |
| | | diuron | 250–1600 |
| | | isoprotoron | 250–1600 |
| | phenols | | 100–700 |
| | | bromoxynil | 100–700 |
| | chloridazon | | 500–4000 |
| | triazines | | 250–4000 |
| | | atrazine | 250–4000 |
| | | terbutylazine | 250–4000 |
| | triazinone | | 30–300 |
| | | metribuzin | 30–300 |
| B13 Synergists | | | 500–1500 |
| | oxiranes | | 500–1500 |
| | | tridiphane | 500–1500 |
| B14 Growth substances | | | 25–1200 |
| | aryloxyalkanoic acids | | 50–1200 |
| | | fluoroxypyr | 50–400 |
| | | MCPA | 400–1200 |

TABLE 2-continued

| Component B | Class of active ingredient | Active ingredient | Rate of application (g/ha) |
|---|---|---|---|
| | | mecoprop-P | 400–1200 |
| | benzoic acids | | 75–800 |
| | | dicamba | 75–800 |
| | quinolinecarboxylic acids | | 25–600 |
| | | quinclorac | 25–600 |
| B16 Various other herbicides | | triaziflam | 50–750 |

[a]If appropriate, 10–50 g/ha cloquintocet may also be added.

USE EXAMPLES

The mixtures according to the invention were applied pre- or post-emergence (foliar treatment). The herbicidal compounds of component B were applied in the formulation in which they are present as commercially available product.

Some of the experiments were greenhouse experiments and some were field trials on mini plots (on a site with sandy loam (pH 6.2 to 7.0) or sandy clay (pH 5.0 to 6.7) as the soil).

The harmful plants differed with regard to size and developmental state; on average, they were 5 to 20 cm long, depending on the growth habit.

The herbicidally active compounds of components A) and B) were applied in succession or jointly, in the latter case in some cases as a tank mix and in some cases as a readymix, in the form of emulsions, aqueous solutions or suspensions, the vehicle being water (300–400 l/ha). In the case of the field trials, application was effected with the aid of a mobile plot sprayer.

The test period extended over 3 to 8 weeks, and the stands were also observed at later points in time.

Damage by the herbicidal compositions was evaluated with reference to a scale of 0% to 100% in comparison with untreated control plots. 0 means no damage and 100 means complete destruction of the plants.

The following examples will demonstrate the action of the herbicidal compositions which can be used according to the invention, without excluding the possibility of other uses.

In these examples, the value E at which only an additive effect of the individual active ingredients is to be expected was calculated by the method of S. R. Colby (Calculating synergistic and antagonistic responses of herbicide combinations, Weeds 15, 20 pp (1967).

This was done using the formula $$E = X + Y - \frac{XY}{100}$$

where
X=Percentage of the herbicidal action of component A) at an application rate of a;
Y=Percentage of the herbicidal action of component B) at an application rate of b;
E=expected herbicidal action of component A)+B) at rates of application a+b (in %).

If the value observed exceeds the value E calculated in accordance with Colby's formula, then synergism is present.

The herbicidal mixtures according to the invention exert a greater herbicidal action than would have been expected according to Colby on the basis of the observed effects of the individual components when used alone.

The results of the tests are shown in Tables 3 to 82 below.

In these studies, the following plants were used:

| Scientific name | Common name |
|---|---|
| Abutilon theophrasti | Chinese lantern |
| Alopecuros myosuroides | Slender foxtail |
| Amaranthus retroflexus | Redroot pigweed |
| Anthemis mixta | Camomile |
| Bidens pilosa | Common blackjack |
| Brachiaria plantaginea | Alexander grass |
| Chenopodium album | Lambsquarters |
| Cyperus iria | — |
| Cyperus species | Cyprus grass species |
| Digitaria adscendens | Crab grass |
| Digitaria sanguinalis | Hairy fingergrass |
| Echinochloa crus-galli | Common barnyard grass |
| Galium aparine | Bedstraw, catchweed |
| Geranium carolinianum | Carolina geranium |
| Ipomoea acuminata | Blue morning-glory |
| Ipomoea lacunosa | — |
| Ipomoea purpurea var. diversifolia | — |
| Ipomoea ssp. [sic] | Morning-glory species |
| Lolium perenne | Perennial rye grass |
| Panicum miliaceum | Prozo millet |
| Phalaris spec. | Canary grass species |
| Richardia brasiliensis | — |
| Setaria faberi | Giant foxtail |
| Setaria viridis | Green foxtail |
| Sorghum bicolor | Common sorghum |
| Sorghum halepense | Johnson grass |
| Stellaria media | Common chickweed |
| Triticum aestivum | Winter wheat |
| Veronica ssp. [sic] | Speedwell species |
| Zea mays | Maize |

TABLE 3

Herbicidal action of compound Ia.3 and "cycloxydim" (B1) on *Chenopodium album* in the field (post-emergence treatment)

| Rate of application (g/ha a.s.) | | | |
|---|---|---|---|
| Ia.3 | Cycloxydim | Damage (%) | Colby value E |
| 50 | — | 92 | — |
| — | 100 | 0 | — |
| 50 | 100 | 98 | 92 |

TABLE 4

Herbicidal action of compound Ia.3 and "cycloxydim" (B1) on *Digitaria sanguinalis* in the field (post-emergence treatment)

Rate of application (g/ha a.s.)

| Ia.3 | Cycloxydim | Damage (%) | Colby value E |
|---|---|---|---|
| 50 | — | 57 | — |
| — | 100 | 81 | — |
| 50 | 100 | 98 | 92 |

TABLE 5

Herbicidal action of compound Ia.3 and "sethoxydim" (B1) on *Abutilon theophrasti* in the field (post-emergence treatment)

Rate of application (g/ha a.s.)

| Ia.3 | Sethoxydim | Damage (%) | Colby value E |
|---|---|---|---|
| 50 | — | 85 | — |
| — | 160 | 0 | — |
| 50 | 160 | 94 | 85 |

TABLE 6

Herbicidal action of compound Ia.3 and "sethoxydim" (B1) on *Setaria viridis* in the field (post-emergence treatment)

Rate of application (g/ha a.s.)

| Ia.3 | Sethoxydim | Damage (%) | Colby value E |
|---|---|---|---|
| 100 | — | 75 | — |
| — | 160 | 93 | — |
| 100 | 160 | 99 | 98 |

TABLE 7

Herbicidal action of compound Ia.3 and "clodinafop-propargyl + cloquintocet" (B1) on *Alopecurus myosuroides* in the field (post-emergence treatment)

Rate of application (g/ha a.s.)

| Ia.3 | clodinafop-propargyl + cloquintocet | Damage (%) | Colby value E |
|---|---|---|---|
| 7.5 | — | 10 | — |
| — | 40 | 63 | — |
| 75 | 40 | 94 | 67 |

TABLE 8

Herbicidal action of compound Ia.3 and "fenoxaprop-ethyl" (B1) on *Alopecurus myosuroides* in the field (post-emergence treatment)

Rate of application (g/ha a.s.)

| Ia.3 | fenoxaprop-ethyl | Damage (%) | Colby value E |
|---|---|---|---|
| 75 | — | 10 | — |
| — | 83 | 82 | — |
| 75 | 83 | 94 | 84 |

TABLE 9

Herbicidal action of compound Ia.3 and "fenoxaprop-ethyl" (B1) on *Galium aparine* in the field (post-emergence treatment)

Rate of application (g/ha a.s.)

| Ia.3 | fenoxaprop-ethyl | Damage (%) | Colby value E |
|---|---|---|---|
| 75 | — | 63 | — |
| — | 83 | 0 | — |
| 75 | 83 | 75 | 63 |

TABLE 10

Herbicidal action of compound Ia.3 and "fenoxaprop-P-ethyl" (B1) on *Amaranthus retroflexus* in the greenhouse (post-emergence treatment)

Rate of application (g/ha a.s.)

| Ia.3 | fenoxaprop-ethyl | Damage (%) | Colby value E |
|---|---|---|---|
| 15.6 | — | 80 | — |
| — | 31.2 | 0 | — |
| 15.6 | 31.2 | 95 | 80 |

TABLE 11

Herbicidal action of compound Ia.33 and "imazapyr" (B1) on *Alopecurus myosuroides* in the greenhouse (post-emergence treatment)

Rate of application (g/ha a.s.)

| Ia.33 | imazapyr | Damage (%) | Colby value E |
|---|---|---|---|
| 15.6 | — | 40 | — |
| — | 250 | 90 | — |
| 15.6 | 250 | 95 | 94 |

TABLE 12

Herbicidal action of compound Ia.33 and "imazapyr" (B1) on Ipomoea ssp. [sic] in the greenhouse (post-emergence treatment)

| Rate of application (g/ha a.s.) | | | |
|---|---|---|---|
| Ia.33 | imazapyr | Damage (%) | Colby value E |
| 3.9 | — | 50 | — |
| — | 62.5 | 85 | — |
| 3.9 | 62.5 | 95 | 93 |

TABLE 13

Herbicidal action of compound Ia.3 and "imazaquin" (B2) on *Bidens pilosa* in the field (post-emergence treatment)

| Rate of application (g/ha a.s.) | | | |
|---|---|---|---|
| Ia.3 | imazaquin | Damage (%) | Colby value E |
| 75 | — | 30 | — |
| — | 150 | 45 | — |
| 75 | 150 | 95 | 62 |

TABLE 14

Herbicidal action of compound Ia.3 and "imazamethabenz" (B2) on *Stellaria media* in the field (post-emergence treatment)

| Rate of application (g/ha a.s.) | | | |
|---|---|---|---|
| Ia.3 | imazamethabenz | Damage (%) | Colby value E |
| 75 | — | 91 | — |
| — | 525 | 0 | — |
| 75 | 525 | 99 | 91 |

TABLE 15

Herbicidal action of compound Ia.3 and "imazethapyr" (B2) on *Ipomoea acuminata* in the field (post-emergence treatment)

| Rate of application (g/ha a.s.) | | | |
|---|---|---|---|
| Ia.3 | imazethapyr | Damage (%) | Colby value E |
| 75 | — | 25 | — |
| — | 70 | 33 | — |
| 75 | 70 | 95 | 50 |

TABLE 16

Herbicidal action or compound Ia.3 and "imazethapyr" (B2) on *Ipomoea purpurea* var. *diversifolia* in the field (post-emergence treatment)

| Rate of application (g/ha a.s.) | | | |
|---|---|---|---|
| Ia.3 | imazethapyr | Damage (%) | Colby value E |
| 75 | — | 93 | — |
| — | 70 | 58 | — |
| 75 | 70 | 99 | 97 |

TABLE 17

Herbicidal action of compound Ia.33 and "pyrithiobac-sodium" (B2) on *Echinochloa crus-galli* in the greenhouse (post-emergence treatment)

| Rate of application (g/ha a.s.) | | | |
|---|---|---|---|
| Ia.33 | pyrithiobac-sodium | Damage (%) | Colby value E |
| 1.9 | — | 55 | — |
| — | 7.8 | 10 | — |
| 1.9 | 7.8 | 75 | 59 |

TABLE 18

Herbicidal action of compound Ia.33 and "metosulam" (B2) on Veronica ssp. [sic] in the greenhouse (post-emergence treatment)

| Rate of application (g/ha a.s.) | | | |
|---|---|---|---|
| Ia.33 | metosulam | Damage (%) | Colby value E |
| 62.5 | — | 20 | — |
| — | 1.9 | 40 | — |
| 62.5 | 1.9 | 75 | 52 |

TABLE 19

Herbicidal action of compound Ia.33 and "halosulfuron-methyl" (B2) on *Alopecurus myosuroides* in the greenhouse (post-emergence treatment)

| Rate of application (g/ha a.s.) | | | |
|---|---|---|---|
| Ia.33 | halosulfuron-methyl | Damage (%) | Colby value E |
| 62.5 | — | 40 | — |
| — | 31.2 | 45 | — |
| 62.5 | 31.2 | 85 | 67 |

TABLE 20

Herbicidal action of compound Ia.33 and "halosulfuron-methyl" (B2) on *Amaranthus retroflexus* in the greenhouse (post-emergence treatment)

| Rate of application (g/ha a.s.) | | | |
|---|---|---|---|
| Ia.33 | halosulfuron-methyl | Damage (%) | Colby value E |
| 7.8 | — | 70 | — |
| — | 7.8 | 80 | — |
| 7.8 | 7.8 | 98 | 94 |

TABLE 21

Herbicidal action of compound Ia.33 and "nicosulfuron" (B2) on *Ipomoea lacunosa* in the field (post-emergence treatment)

| Rate of application (g/ha a.s.) | | | |
|---|---|---|---|
| Ia.33 | nicosulfuron | Damage (%) | Colby value E |
| 75 | — | 69 | — |
| — | 35 | 39 | — |
| 75 | 35 | 90 | 81 |

TABLE 22

Herbicidal action of compound Ia.50 and "nicosulfuron" (B2) on *Amaranthus retroflexus* in the greenhouse (post-emergence treatment)

| Rate of application (g/ha a.s.) | | | |
|---|---|---|---|
| Ia.50 | nicosulfuron | Damage (%) | Colby value E |
| 3.9 | — | 10 | — |
| — | 1.9 | 65 | — |
| 3.9 | 1.9 | 80 | 69 |

TABLE 23

Herbicidal action of compound Ia.33 and "N-[[[4-methoxy-6-(trifluoromethyl)-1,3,5-triazin-2-yl]amino]carbonyl]-2-(trifluoromethyl)benzene-sulfonamide" (B2) on *Setaria faberi* in the field (post-emergence treatment)

| Rate of application (g/ha a.s.) | | | |
|---|---|---|---|
| Ia.33 | N-[[[4-methoxy-6-(trifluoromethyl)-1,3,5-triazin-2-yl]amino]carbonyl]-2-(trifluoromethyl)-benzene-sulfonamide | Damage (%) | Colby value E |
| 75 | — | 65 | — |
| — | 50 | 0 | — |
| 75 | 50 | 73 | 65 |

TABLE 24

Herbicidal action of compound Ia.3 and "2,4-D" (B4) on *Abutilon theophrasti* in the greenhouse (post-emergence treatment)

| Rate of application (g/ha a.s.) | | | |
|---|---|---|---|
| Ia.3 | 2,4-D | Damage (%) | Colby value E |
| 15.6 | — | 70 | — |
| — | 62.5 | 40 | — |
| 15.6 | 62.5 | 85 | 82 |

TABLE 25

Herbicidal action of compound Ia.3 and "2,4-D" (B4) on *Amaranthus retroflexus* in the greenhouse (post-emergence treatment)

| Rate of application (g/ha a.s.) | | | |
|---|---|---|---|
| Ia.3 | 2,4-D | Damage (%) | Colby value E |
| 15.6 | — | 55 | — |
| — | 62.5 | 20 | — |
| 15.6 | 62.5 | 70 | 64 |

TABLE 26

Herbicidal action of compound Ia.3 and "2,4-D" (B4) on *Phalaris spec.* in the field (post-emergence treatment)

| Rate of application (g/ha a.s.) | | | |
|---|---|---|---|
| Ia.3 | 2,4-D | Damage (%) | Colby value E |
| 75 | — | 20 | — |
| — | 500 | 20 | — |
| 75 | 500 | 43 | 36 |

TABLE 27

Herbicidal action of compound Ia.3 and "isoxaflutole" (B6) on ipomoea ssp. [sic] in the greenhouse (post-emergence treatment)

| Rate of application (g/ha a.s.) | | | |
|---|---|---|---|
| Ia.3 | isoxaflutole | Damage (%) | Colby value E |
| 31.2 | — | 75 | — |
| — | 62.5 | 55 | — |
| 31.2 | 62.5 | 90 | 89 |

TABLE 28

Herbicidal action of compound Ia.3 and "isoxaflutole"
(B6) on *Setaria viridis* in the greenhouse
(post-emergence treatment)

| Rate of application (g/ha a.s.) | | | |
|---|---|---|---|
| Ia.3 | isoxaflutole | Damage (%) | Colby value E |
| 15.6 | — | 80 | — |
| — | 31.2 | 30 | — |
| 15.6 | 31.2 | 90 | 86 |

TABLE 29

Herbicidal action of compound Ia.3 and "sulcotrione"
(B6) on *Ipomoea acuminata* in the field (post-emergence treatment)

| Rate of application (g/ha a.s.) | | | |
|---|---|---|---|
| Ia.3 | sulcotrione | Damage (%) | Colby value E |
| 75 | — | 25 | — |
| — | 300 | 86 | — |
| 75 | 300 | 98 | 90 |

TABLE 30

Herbicidal action of compound Ia.50 and "sulcotrione"
(B6) on *Amaranthus retroflexus* in the greenhouse
(post-emergence treatment)

| Rate of application (g/ha a.s.) | | | |
|---|---|---|---|
| Ia.50 | sulcotrione | Damage (%) | Colby value E |
| 31.2 | — | 60 | — |
| — | 250 | 45 | — |
| 31.2 | 250 | 80 | 78 |

TABLE 31

Herbicidal action of compound Ia.3 and "glyphosate"
(B7) on *Geranium carolinianum* in the field
(post-emergence treatment)

| Rate of application (g/ha a.s.) | | | |
|---|---|---|---|
| Ia.3 | glyphosate | Damage (%) | Colby value E |
| 150 | — | 30 | — |
| — | 840 | 97 | — |
| 150 | 840 | 100 | 98 |

TABLE 32

Herbicidal action of compound Ia.33 and "glyphosate"
(B7) on *Sorghum halepense* in the field
(post-emergence treatment)

| Rate of application (g/ha a.s.) | | | |
|---|---|---|---|
| Ia.33 | glyphosate | Damage (%) | Colby value E |
| 75 | — | 78 | — |
| — | 840 | 74 | — |
| 75 | 840 | 97 | 94 |

TABLE 33

Herbicidal action of compound Ia.3 and
"glufosinate-ammonium" (B8) on
*Digitaria adscendens* in the field
(post-emergence treatment)

| Rate of application (g/ha a.s.) | | | |
|---|---|---|---|
| Ia.3 | glufosinate-ammonium | Damage (%) | Colby value E |
| 75 | — | 90 | — |
| — | 400 | 75 | — |
| 75 | 400 | 100 | 98 |

TABLE 34

Herbicidal action of compound Ia.33 and
"glufosinate-ammonium" (B8) on
*Echinochloa crus-galli* in the greenhouse
(post-emergence treatment)

| Rate of application (g/ha a.s.) | | | |
|---|---|---|---|
| Ia.33 | glufosinate-ammonium | Damage (%) | Colby value E |
| 15.6 | — | 90 | — |
| — | 15.6 | 0 | — |
| 15.6 | 15.6 | 98 | 90 |

TABLE 35

Herbicidal action of compound Ia.3 and
"glufosinate-ammonium" (B8) on
*Ipomoea acuminata* in the field
(post-emergence treatment)

| Rate of application (g/ha a.s.) | | | |
|---|---|---|---|
| Ia.3 | glufosinate-ammonium | Damage (%) | Colby value E |
| 75 | — | 25 | — |
| — | 400 | 75 | — |
| 75 | 400 | 98 | 81 |

TABLE 36

Herbicidal action of compound Ia.33 and "glufosinate-ammonium" (B8) on *Setaria faberi* in the greenhouse (post-emergence treatment)

| Rate of application (g/ha a.s.) | | | |
|---|---|---|---|
| Ia.33 | glufosinate-ammonium | Damage (%) | Colby value E |
| 7.8 | — | 90 | — |
| — | 31.2 | 65 | — |
| 7.8 | 31.2 | 98 | 96 |

TABLE 37

Herbicidal action of compound Ia.3 and "flufenacet" (B3) on *Digitaria adscendens* in the field (post-emergence treatment)

| Rate of application (g/ha a.s.) | | | |
|---|---|---|---|
| Ia.3 | flufenacet | Damage (%) | Colby value E |
| 75 | — | 90 | — |
| — | 600 | 58 | — |
| 75 | 600 | 100 | 96 |

TABLE 38

Herbicidal action of compound Ia.3 and "dimethenamid" (B9) on *Amaranthus retroflexus* in the greenhouse (pre-emergence treatment)

| Rate of application (g/ha a.s.) | | | |
|---|---|---|---|
| Ia.3 | Dimethenamid | Damage (%) | Colby-value E |
| 31.2 | — | 40 | — |
| — | 125 | 80 | — |
| 31.2 | 125 | 100 | 88 |

TABLE 39

Herbicidal action of compound Ia.3 and "dimethenamid" (B9) on *Cyperus iria* in the greenhouse (pre-emergence treatment)

| Rate of application (g/ha a.s.) | | | |
|---|---|---|---|
| Ia.3 | Dimethenamid | Damage (%) | Colby-value E |
| 31.2 | — | 50 | — |
| — | 62.5 | 95 | — |
| 31.2 | 62.5 | 100 | 98 |

TABLE 40

Herbicidal action of compound Ia.3 and "dimethenamid" (B9) on *Digitaria sanguinalis* in the greenhouse (pre-emergence treatment)

| Rate of application (g/ha a.s.) | | | |
|---|---|---|---|
| Ia.3 | Dimethenamid | Damage (%) | Colby value E |
| 62.5 | — | 60 | — |
| — | 125 | 80 | — |
| 62.5 | 125 | 98 | 92 |

TABLE 41

Herbicidal action of compound Ia.33 and "dimethenamid" (B9) on *Panicum miliaceum* in the field (post-emergence treatment)

| Rate of application (g/ha a.s.) | | | |
|---|---|---|---|
| Ia.33 | dimethenamid | Damage (%) | Colby value E |
| 50 | — | 87 | — |
| — | 841 | 23 | — |
| 50 | 841 | 94 | 90 |

TABLE 42

Herbicidal action of compound Ia.33 and "dimethenamid" (B9) on *Sorghum halepense* in the field (post-emergence treatment)

| Rate of application (g/ha a.s.) | | | |
|---|---|---|---|
| Ia.33 | dimethenamid | Damage (%) | Colby value E |
| 75 | — | 78 | — |
| — | 1120 | 7 | — |
| 75 | 1120 | 90 | 80 |

TABLE 43

Herbicidal action of compound Ia.33 and "dimethenamid" (B9) on *Veronica* ssp. [sic] in the greenhouse (post-emergence treatment)

| Rate of application (g/ha a.s.) | | | |
|---|---|---|---|
| Ia.33 | Dimethenamid | Damage (%) | Colby value E |
| 15.6 | — | 60 | — |
| — | 500 | 70 | — |
| 15.6 | 500 | 90 | 88 |

TABLE 44

Herbicidal action of compound Ia.52 and "dimethenamid"
(B9) on *Amaranthus retroflexus* in the greenhouse
(post-emergence treatment)

Rate of application
(g/ha a.s.)

| Ia.52 | Dimethenamid | Damage (%) | Colby value E |
|---|---|---|---|
| 62.5 | — | 75 | — |
| — | 500 | 10 | — |
| 62.5 | 500 | 100 | 78 |

TABLE 45

Herbicidal action of compound Ia.52 and "dimethenamid"
(B9) on *Veronica ssp.* [sic] in the greenhouse
(post-emergence treatment)

Rate of application
(g/ha a.s.)

| Ia.52 | Dimethenamid | Damage (%) | Colby value E |
|---|---|---|---|
| 15.6 | — | 40 | — |
| — | 500 | 70 | — |
| 15.6 | 500 | 100 | 82 |

TABLE 46

Herbicidal action of compound Ia.33 and "acetochlor"
(B9) on *Abutilon theophrasti* in the greenhouse
(post-emergence treatment)

Rate of application
(g/ha a.s.)

| Ia.33 | acetochlor | Damage (%) | Colby value E |
|---|---|---|---|
| 7.8 | — | 90 | — |
| — | 31.2 | 0 | — |
| 7.8 | 31.2 | 100 | 90 |

TABLE 47

Herbicidal action of compound Ia.3 and "S-metolachlor"
(B9) on *Digitaria sanguinalis* in the greenhouse
(pre-emergence treatment)

Rate of application (g/ha a.s.)

| Ia.3 | S-Metolachlor | Damage (%) | Colby value E |
|---|---|---|---|
| 62.5 | — | 60 | — |
| — | 125 | 50 | — |
| 62.5 | 125 | 85 | 80 |

TABLE 48

Herbicidal action of compound Ia.3 and "S-metolachlor"
(B9) on *Echinochloa crus-galli* in the greenhouse
(pre-emergence treatment)

Rate of application
(g/ha a.s.)

| Ia.3 | S-Metolachlor | Damage (%) | Colby value E |
|---|---|---|---|
| 62.5 | — | 60 | — |
| — | 62.5 | 65 | — |
| 62.5 | 62.5 | 98 | 86 |

TABLE 49

Herbicidal action of compound Ia.3 and "S-metolachlor"
(B9) on *Setaria viridis* in the greenhouse
(pre-emergence treatment)

Rate of application
(g/ha a.s.)

| Ia.3 | S-Metolachlor | Damage (%) | Colby value E |
|---|---|---|---|
| 15.6 | — | 20 | — |
| — | 62.5 | 70 | — |
| 15.6 | 62.5 | 85 | 76 |

TABLE 50

Herbicidal action of compound Ia.33 and
"S-metolachlor" (B9) on *Ipomoea* ssp. [sic] in the
greenhouse (post-emergence treatment)

Rate of application
(g/ha a.s.)

| Ia.33 | S-Metolachlor | Damage (%) | Colby value E |
|---|---|---|---|
| 62.5 | — | 80 | — |
| — | 62.5 | 0 | — |
| 62.5 | 62.5 | 90 | 80 |

TABLE 51

Herbicidal action of compound Ia.33 and
"S-metolachlor" (B9) on *Veronica ssp.*
[sic] in the greenhouse
(post-emergence treatment)

Rate of application
(g/ha a.s.)

| Ia.33 | S-Metolachlor | Damage (%) | Colby value E |
|---|---|---|---|
| 62.5 | — | 80 | — |
| — | 125 | 0 | — |
| 62.5 | 125 | 98 | 80 |

TABLE 52

Herbicidal action of compound Ia.16 and "benthiocarb"
(B9) on *Cyperus iria* in the field
(post-emergence treatment)

Rate of application
(g/ha a.s.)

| Ia.16 | benthiocarb | Damage (%) | Colby value E |
|---|---|---|---|
| 75 | — | 60 | — |
| — | 3000 | 50 | — |
| 75 | 3000 | 92 | 80 |

TABLE 53

Herbicidal action of compound Ia.3 and "pendimethalin"
(B10) on *Brachiaria plantaginea* in the field
(post-emergence treatment)

Rate of application
(g/ha a.s.)

| Ia.3 | pendimethalin | Damage (%) | Colby value E |
|---|---|---|---|
| 75 | — | 96 | — |
| — | 990 | 0 | — |
| 75 | 990 | 98 | 96 |

TABLE 54

Herbicidal action of compound Ia.3 and "acifluorfen"
(B11) on *Galium aparine* in the field
(post-emergence treatment)

Rate of application
(g/ha a.s.)

| Ia.3 | acifluorfen | Damage (%) | Colby value E |
|---|---|---|---|
| 75 | — | 60 | — |
| — | 100 | 48 | — |
| 75 | 100 | 95 | 79 |

TABLE 55

Herbicidal action of compound Ia.33 and
"carfentrazone-ethyl" (B11) on *Amaranthus retroflexus*
in the greenhouse (post-emergence treatment)

Rate of application
(g/ha a.s.)

| Ia.33 | carfentrazone-ethyl | Damage (%) | Colby value E |
|---|---|---|---|
| 1.9 | — | 30 | — |
| — | 0.9 | 60 | — |
| 1.9 | 0.9 | 90 | 72 |

TABLE 56

Herbicidal action of compound Ia.3 and
"carfentrazone-ethyl" (B11) on *Anthemis mixta*
in the field (post-emergence treatment)

Rate of application
(g/ha a.s.)

| Ia.3 | carfentrazone-ethyl | Damage (%) | Colby value E |
|---|---|---|---|
| 75 | — | 68 | — |
| — | 30 | 0 | — |
| 75 | 30 | 91 | 68 |

TABLE 57

Herbicidal action of compound Ia.33 and
"cinidon-ethyl" (B11) on
*Galium aparine* in the field
(post-emergence treatment)

Rate of application
(g/ha a.s.)

| Ia.33 | cinidon-ethyl | Damage (%) | Colby value E |
|---|---|---|---|
| 1.9 | — | 20 | — |
| — | 7.8 | 90 | — |
| 1.9 | 7.8 | 100 | 92 |

TABLE 58

Herbicidal action of compound Ia.3 and "pyridate"
(B12) on *Bidens pilosa* in the field
(post-emergence treatment)

Rate of application
(g/ha a.s.)

| Ia.3 | pyridate | Damage (%) | Colby value E |
|---|---|---|---|
| 75 | — | 25 | — |
| — | 450 | 25 | — |
| 75 | 450 | 96 | 44 |

TABLE 59

Herbicidal action of Ia.3 and "pyridate" (B12) on
*Setaria faberi* in the field
(post-emergence treatment)

Rate of application
(g/ha a.s.)

| Ia.3 | pyridate | Damage (%) | Colby value E |
|---|---|---|---|
| 75 | — | 99 | — |
| — | 450 | 0 | — |
| 75 | 450 | 100 | 99 |

TABLE 60

Herbicidal action of compound Ia.3 and "bentazone" (B12) on *Richardia brasiliensis* in the field (post-emergence treatment)

Rate of application (g/ha a.s.)

| Ia.3 | Bentazone | Damage (%) | Colby value E |
|---|---|---|---|
| 75 | — | 70 | — |
| — | 1440 | 77 | — |
| 75 | 1440 | 99 | 93 |

TABLE 61

Herbicidal action of compound Ia.3 and "paraquat-dichloride" (B12) on *Lolium perenne* in the field (post-emergence treatment)

Rate of application (g/ha a.s.)

| Ia.3 | paraquat-dichloride | Damage (%) | Colby value E |
|---|---|---|---|
| 75 | — | 10 | — |
| — | 400 | 97 | — |
| 75 | 400 | 100 | 97 |

TABLE 62

Herbicidal action of compound Ia.33 and "diuron" (B12) on *Alopecurus myosuroides* in the greenhouse (post-emergence treatment)

Rate of application (g/ha a.s.)

| Ia.33 | diuron | Damage (%) | Colby value E |
|---|---|---|---|
| 62.5 | — | 40 | — |
| — | 250 | 80 | — |
| 62.5 | 250 | 95 | 88 |

TABLE 63

Herbicidal action of compound Ia.3 and "isoproturon" (B12) on *Stellaria media* in the field (post-emergence treatment)

Rate of application (g/ha a.s.)

| Ia.3 | isoproturon | Damage (%) | Colby value E |
|---|---|---|---|
| 75 | — | 91 | — |
| — | 1000 | 94 | — |
| 75 | 1000 | 100 | 99 |

TABLE 64

Herbicidal action of compound Ia.3 and "bromoxynil" (B12) on *Galium aparine* in the field (post-emergence treatment)

Rate of application (g/ha a.s.)

| Ia.3 | bromoxynil | Damage (%) | Colby value E |
|---|---|---|---|
| 75 | — | 60 | — |
| — | 470 | 84 | — |
| 75 | 470 | 98 | 94 |

TABLE 65

Herbicidal action of compound Ia.3 and "chloridazon" (B12) on *Ipomoea purpurea* var. *diversifolia* in the field (post-emergence treatment)

Rate of application (g/ha a.s.)

| Ia.3 | chloridazon | Damage (%) | Colby value E |
|---|---|---|---|
| 75 | — | 94 | — |
| — | 1720 | 40 | — |
| 75 | 1720 | 100 | 96 |

TABLE 66

Herbicidal action of compound Ia.3 and "atrazine" (B12) on *Abutilon theophrasti* in the field (post-emergence treatment)

Rate of application (g/ha a.s.)

| Ia.3 | atrazine | Damage (%) | Colby value E |
|---|---|---|---|
| 75 | — | 85 | — |
| — | 1120 | 32 | — |
| 75 | 1120 | 96 | 90 |

TABLE 67

Herbicidal action of compound Ia.3 and "atrazine" (B12) on *Setaria faberi* in the field (post-emergence treatment)

Rate of application (g/ha a.s.)

| Ia.3 | atrazine | Damage (%) | Colby value E |
|---|---|---|---|
| 75 | — | 95 | — |
| — | 1120 | 20 | — |
| 75 | 1120 | 99 | 96 |

TABLE 68

Herbicidal action of compound Ia.33 and "atrazine" (B12) on *Sorghum bicolor* in the field (post-emergence treatment)

| Rate of application (g/ha a.s.) | | | |
|---|---|---|---|
| Ia.33 | atrazine | Damage (%) | Colby value E |
| 75 | — | 78 | — |
| — | 840 | 27 | — |
| 75 | 840 | 90 | 84 |

TABLE 69

Herbicidal action of compound Ia.3 and "metribuzin" (B12) on *Bidens pilosa* in the field (post-emergence treatment)

| Rate of application (g/ha a.s.) | | | |
|---|---|---|---|
| Ia.3 | metribuzin | Damage (%) | Colby value E |
| 75 | — | 25 | — |
| — | 200 | 38 | — |
| 75 | 200 | 73 | 54 |

TABLE 70

Herbicidal action of compound Ia.3 and "metribuzin" (B12) on *Cyperus* species in the field (post-emergence treatment)

| Rate of application (g/ha a.s.) | | | |
|---|---|---|---|
| Ia.3 | metribuzin | Damage (%) | Colby value E |
| 75 | — | 5 | — |
| — | 200 | 50 | — |
| 75 | 200 | 75 | 53 |

TABLE 71

Herbicidal action of compound Ia.3 and "MCPA" (B14) on *Cyperus* species in the field (post-emergence treatment)

| Rate of application (g/ha a.s.) | | | |
|---|---|---|---|
| Ia.3 | MCPA | Damage (%) | Colby value E |
| 75 | — | 0 | — |
| — | 600 | 5 | — |
| 75 | 600 | 48 | 5 |

TABLE 72

Herbicidal action of compound Ia.16 and "dicamba" (B14) on *Amaranthus retroflexus* in the field (post-emergence treatment)

| Rate of application (g/ha a.s.) | | | |
|---|---|---|---|
| Ia.16 | dicamba | Damage (%) | Colby value E |
| 100 | — | 96 | — |
| — | 280 | 25 | — |
| 100 | 280 | 100 | 97 |

TABLE 73

Herbicidal action of compound Ia.33 and "dicamba" (B14) on *Sorghum bicolor* in the field (post-emergence treatment)

| Rate of application (g/ha a.s.) | | | |
|---|---|---|---|
| Ia.33 | dicamba | Damage (%) | Colby value E |
| 75 | — | 78 | — |
| — | 560 | 17 | — |
| 75 | 560 | 89 | 81 |

TABLE 74

Herbicidal action of compound Ia.3 and "quinclorac" (B14) on *Ipomoea* ssp. [sic] in the greenhouse (post-emergence treatment)

| Rate of application (g/ha a.s.) | | | |
|---|---|---|---|
| Ia.3 | Quinclorac | Damage (%) | Colby value E |
| 31.2 | — | 75 | — |
| — | 250 | 70 | — |
| 31.2 | 250 | 100 | 93 |

TABLE 75

Herbicidal action of compound Ia.3 and "quinclorac" (B14) on *Veronica* ssp. [sic] in the greenhouse (post-emergence treatment)

| Rate of application (g/ha a.s.) | | | |
|---|---|---|---|
| Ia.3 | Quinclorac | Damage (%) | Colby value E |
| 31.2 | — | 80 | — |
| — | 500 | 80 | — |
| 31.2 | 500 | 100 | 96 |

TABLE 76

Herbicidal action of compound Ia.3, "nicosulfuron" (B2) and "dicamba" (B14) on *Ipomoea acuminata* in the field (post-emergence treatment)

| Rate of application (g/ha a.s.) | | | |
|---|---|---|---|
| Ia.3 | nicosulfuron + dicamba | Damage (%) | Colby value E |
| 75 | — | 23 | — |
| — | 20 + 192 | 89 | — |
| 75 | 20 + 192 | 97 | 92 |

TABLE 77

Herbicidal action of compound Ia.3, "diflufenzopyr" (B5) and "dicamba" (B14) on *Echinochloa crus-galli* in the field (post-emergence treatment)

| Rate of application (g/ha a.s.) | | | |
|---|---|---|---|
| Ia.3 | diflufenzopyr + dicamba | Damage (%) | Colby value E |
| 75 | — | 98 | — |
| — | 56 + 140 | 5 | — |
| 75 | 56 + 140 | 99 | 98 |

TABLE 78

Herbicidal action of compound Ia.33, "diflufenzopyr" (B5) and "dicamba" (B14) on *Sorghum halepense* in the field (post-emergence treatment)

| Rate of application (g/ha a.s.) | | | |
|---|---|---|---|
| Ia.33 | diflufenzopyr + dicamba | Damage (%) | Colby value E |
| 75 | — | 78 | — |
| — | 60 + 150 | 27 | — |
| 75 | 60 + 150 | 90 | 84 |

TABLE 79

Herbicidal action of compound Ia.33, "dimethenamide" (B9) and "atrazine" (B12) on *Sorghum halepense* in the field (post-emergence treatment)

| Rate of application (g/ha a.s.) | | | |
|---|---|---|---|
| Ia.33 | dimethenamide + atrazine | Damage (%) | Colby value E |
| 75 | — | 78 | — |
| — | 840 + 960 | 5 | — |
| 75 | 840 + 960 | 97 | 79 |

TABLE 80

Herbicidal action of compound Ia.3, "bentazone" (B12) and "atrazine" (B12) on *Brachiaria plantaginea* in the field (post-emergence treatment)

| Rate of application (g/ha a.s.) | | | |
|---|---|---|---|
| Ia.3 | bentazone + atrazine | Damage (%) | Colby value E |
| 75 | — | 95 | — |
| — | 800 + 800 | 25 | — |
| 75 | 800 + 800 | 98 | 96 |

TABLE 81

Herbicidal action of compound Ia.33, "atrazine" (B12) and "dicamba" (B14) on *Ipomoea lacunosa* in the field (post-emergence treatment)

| Rate of application (g/ha a.s.) | | | |
|---|---|---|---|
| Ia.33 | atrazine + dicamba | Damage (%) | Colby value E |
| 75 | — | 69 | — |
| — | 920 + 480 | 83 | — |
| 75 | 920 + 480 | 99 | 95 |

TABLE 82

Herbicidal action of compound Ia.33, "atrazine" (B12) and "dicamba" (B12) on *Setaria faberi* in the field (post-emergence treatment)

| Rate of application (g/ha a.s.) | | | |
|---|---|---|---|
| Ia.33 | atrazine + dicamba | Damage (%) | Colby value E |
| 75 | — | 65 | — |
| — | 367 + 193 | 20 | — |
| 75 | 367 + 193 | 89 | 72 |

Further experiments demonstrated that the mixtures according to the invention are crop plant selective (Tables 83 and 84).

TABLE 83

Phytotoxicity of compound Ia.52 and "dimethenamid" (B9) to *Triticum aestivum* in the greenhouse (post-emergence treatment)

| Rate of application (g/ha a.s.) | | |
|---|---|---|
| Ia.52 | Dimethenamide | Phytotoxicity (%) |
| 62.5 | — | 0 |
| — | 500 | 0 |
| 62.5 | 500 | 0 |

TABLE 84

Phytotoxicity of compound Ia.33 and "S-metolachlor" (B9) on *Zea mays* in the greenhouse (post-emergence treatment)

| Rate of application (g/ha a.s.) | | |
|---|---|---|
| Ia.33 | S-Metolachlor | Phytotoxicity (%) |
| 62.5 | — | 0 |
| — | 125 | 0 |
| 62.5 | 125 | 0 |

We claim:

1. A synergistic herbicidal mixture comprising synergistically effective amounts of
   A) at least one 3-heterocyclyl-substituted benzoyl compound of formula I

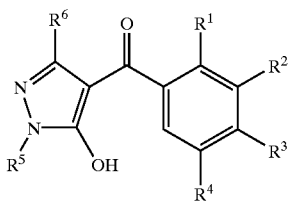

wherein
   $R^1$ is halogen or $C_1$–$C_6$-alkyl;
   $R^3$ is $C_1$–$C_6$-alkylsulfonyl;
   $R^2$ is a heterocyclic radical selected from the group: 4,5-dihydroisoxazol-3-yl, 4,5-dihydroisoxazol-4-yl and 4,5-dihydroisoxazol-5-yl, it being possible for the three radicals mentioned to be unsubstituted or mono- or poly-substituted by halogen, $C_1$–$C_4$-alkyl, $C_1$–$C_4$-alkoxy, $C_1$–$C_4$-haloalkyl, $C_1$–$C_4$-haloalkoxy or $C_1$–$C_4$-alkylthio;
   $R^4$ is hydrogen, halogen or $C_1$–$C_6$-alkyl:
   $R^5$ is $C_1$–$C_6$-alkyl;
   $R^6$ is hydrogen or $C_1$–$C_6$-alkyl;
   or one of its environmentally compatible salts;
   and
   B) at least one herbicidal compound selected from the group consisting of
      B1—alloxydim, clethodim, cloproxydim, cycloxydim, sethoxydim, tralkoxydim, butroxydim, clefoxydim and tepraloxydim;
         clodinafop-propargyl (and, if appropriate, cloquintocet), cyhalofop-butyl, diclofop-methyl, fenoxaprop-ethyl, fenoxaprop-P-ethyl, fenthiaprop-ethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl and quizalofop-tefuryl;
      and their environmentally compatible salts.

2. The mixture defined in claim 1, comprising a compound of formula I wherein
   $R^2$ is isoxazol-5-yl, 3-methyl-isoxazol-5-yl, 4,5-dihydroisoxazol-3-yl, 5-methyl-4,5-dihydroisoxazol-3-yl, 5-ethyl-4,5-dihydroisoxazol-3-yl, or 4,5-dimethyl-4,5-dihydroisoxazol-3-yl.

3. The mixture defined in claim 1, wherein the compound of formula I is 4-[2-chloro-3-(4,5-dihydroisoxazol-3-yl)-4-methyl-sulfonylbenzoyl]-1-methyl-5-hydroxy-1H-pyrazole.

4. The mixture defined in claim 1, wherein the compound of formula I is 4-[2-methyl-3-(4,5-dihydroisoxazol-3-yl)-4-methylsulfonylbenzoyl]-1-methyl-5-hydroxy-1H-pyrazole.

5. The mixture defined in claim 1, wherein component B) comprises fenoxaprop-ethyl.

6. The mixture defined in claim 1, wherein component B) comprises clodinafop (and optionally oloquintocet).

7. The mixture defined in claim 1, comprising, as component B), a herbicidal compound selected from group B1, and one further herbicidal compound.

8. The mixture defined in claim 1, comprising, as component B), a herbicidal compound selected from group B1, and a herbicidal compound selected from the group consisting of propanil, pyridate, pyridafol, benzothiadiazinones, dinitrophenols, dipyridylenes, ureas, phenols, chloridazon, triazines, triazinones, uracils, biscarbamates, aryloxyalkanoic acids, benzoic acids and quinolinecarboxylic acids.

9. The mixture defined in claim 1, comprising components A) and B) in a weight ratio of 1:0.002 to 1:800.

10. The mixture defined in claim 1, comprising components A) and B) in a weight ratio of 1:0.003 to 1:160.

11. A herbicidal composition comprising an effective amount of the mixture defined in claim 1, at least one inert liquid or solid carrier and optionally at least one surfactant.

12. The composition defined in claim 11, comprising components A) and B) in a weight ratio of 1:0.002 to 1:800.

13. The composition defined in claim 11, comprising components A) and B) in a weight ratio of 1:0.003 to 1:160.

14. A process for preparing the composition defined in claim 11, which comprises mixing component A), component B), at least one inert liquid or solid carrier and optionally a surfactant.

15. The mixture defined in claim 1, comprising as component B) at least one herbicidal compound selected from the group consisting of alloxydim, clethodim, cloproxydim, cycloxydim, sethoxydim, tralkoxydim, butroxydim, clefoxydim and tepraloxydim, and comprising components A) and B) in a weight ratio of 1:0.4 to 1:80.

16. The mixture defined in claim 1, comprising as component B) at least one herbicidal compound selected from the group consisting of clodinafop-propargyl and optionally cloquintocet, cyhalofop-butyl, diclofop-methyl, fenoxaprop-ethyl, fenoxaprop-P-ethyl, fenthiaprop-ethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl and quizalofop-tefuryl, and comprising components A) and B) in a weight ratio of 1:0.1 to 1:60.

17. A method of controlling undesired vegetation, which comprises applying an effective amount of the mixture defined in claim 1, before, during and/or after the emergence of undesired plants, and wherein the components A) and B) are applied simultaneously or in succession.

18. The method of claim 17, wherein the mixture is applied to leaves of crop plants and of the undesired plants.

19. The method of claim 17, wherein components A) and B) are applied simultaneously.

20. The method of claim 17, wherein components A) and B) are applied in succession.

21. The method of claim 17, wherein the mixture is applied in an amount of from 2 to 5000 g/ha.

22. The method of claim 17, wherein component A) of the mixture is applied in an amount of from 0.1 to 250 g/ha.

* * * * *